(12) United States Patent
Lewis et al.

(10) Patent No.: US 9,388,929 B2
(45) Date of Patent: Jul. 12, 2016

(54) MALE BAYONET CONNECTOR

(75) Inventors: Peter D. Lewis, Fort Collins, CO (US);
Ravikumar Narayanan, Fort Collins, CO (US); Richard W. Cairns, Longmont, CO (US); Riley M. Phipps, Fort Collins, CO (US)

(73) Assignee: Nordson Corporation, Westlake, OH (US)

( * ) Notice: Subject to any disclaimer, the term of this patent is extended or adjusted under 35 U.S.C. 154(b) by 782 days.

(21) Appl. No.: 12/976,921

(22) Filed: Dec. 22, 2010

(65) Prior Publication Data

US 2011/0204622 A1   Aug. 25, 2011

Related U.S. Application Data

(63) Continuation-in-part of application No. 29/351,665, filed on Dec. 9, 2009.

(60) Provisional application No. 61/289,545, filed on Dec. 23, 2009.

(51) Int. Cl.
*F16L 37/56* (2006.01)
*F16L 37/084* (2006.01)
*A61M 39/10* (2006.01)

(52) U.S. Cl.
CPC .............. *F16L 37/56* (2013.01); *A61M 39/105* (2013.01); *A61M 39/1011* (2013.01);
(Continued)

(58) Field of Classification Search
CPC .......... F16L 37/56; F16L 39/06; F16L 37/565
USPC ................................................. 285/317, 308
See application file for complete search history.

(56) References Cited

U.S. PATENT DOCUMENTS

| 163,261 A | 5/1875 | Ruppenthal |
| 185,896 A | 1/1877 | Curtis |

(Continued)

FOREIGN PATENT DOCUMENTS

| BE | 479098 | 1/1948 |
| DE | 1868896 | 3/1963 |

(Continued)

OTHER PUBLICATIONS

U.S. Appl. No. 29/351,665, filed Dec. 9, 2009, Lewis et al.

(Continued)

*Primary Examiner* — David E Bochna
(74) *Attorney, Agent, or Firm* — Baker & Hostetler LLP

(57) ABSTRACT

A male bayonet connector connects a section of tubing to a female latch connector. The male bayonet connector includes a shaft defining a lumen, a distal end portion, and a proximal end portion. The distal end portion of the shaft has a sealing surface configured to engage a seal member within the female latch connector to create a fluid-tight seal. The shaft defines an annular recess proximal to and adjacent the distal end portion. The annular recess has a proximal chamfered side wall and a distal sidewall perpendicular to the axis of the lumen, which are separated by a band of smaller diameter than the sealing surface. A grip is formed on the male bayonet connector between the proximal end portion and the annular recess. A ratio of a length of the first sealing surface to a distance between the grip and the distal sidewall is such that a side-load force, as imparted on the male bayonet connector, will not break a fluid-tight seal between the sealing surface and the seal member.

27 Claims, 12 Drawing Sheets

(52) U.S. Cl.
CPC ... *F16L 37/0841* (2013.01); *A61M 2039/1027* (2013.01); *A61M 2039/1044* (2013.01); *A61M 2039/1083* (2013.01); *A61M 2039/1088* (2013.01)

(56) References Cited

U.S. PATENT DOCUMENTS

| | | | |
|---|---|---|---|
| 187,982 A | 3/1877 | Pirsson et al. | |
| 200,944 A | 3/1878 | Smith | |
| 235,580 A * | 12/1880 | Smith et al. | 285/317 |
| 327,509 A | 10/1885 | Aldridge | |
| 584,008 A | 6/1887 | Munson | |
| 465,868 A | 12/1891 | List | |
| 707,991 A * | 8/1902 | Wareham | 285/317 |
| 725,421 A | 4/1903 | Dinkins | |
| 727,982 A | 5/1903 | Ludwig | |
| 874,957 A | 12/1907 | Godley | |
| 884,461 A | 4/1908 | Browne | |
| 909,131 A | 1/1909 | Antic | |
| 951,889 A | 3/1910 | Teuer | |
| D42,368 S | 3/1912 | Mossberg | |
| 1,029,819 A | 6/1912 | Nylander | |
| 1,033,187 A | 7/1912 | Metzger | |
| 1,039,354 A | 9/1912 | Bonadio | |
| 1,077,417 A | 11/1913 | McCracken | |
| 1,078,112 A | 11/1913 | Storm | |
| 1,115,945 A | 11/1914 | Kunz | |
| 1,115,989 A | 11/1914 | Thurman | |
| 1,193,446 A | 8/1916 | Wells | |
| 1,239,345 A | 9/1917 | Brown | |
| 1,255,847 A | 2/1918 | Arkin | |
| 1,259,684 A | 3/1918 | Vinten | |
| 1,489,310 A | 4/1924 | Critchlow | |
| 1,526,218 A | 2/1925 | Johnson | |
| 1,578,504 A | 3/1926 | Bronson et al. | |
| 1,587,079 A | 6/1926 | Machino | |
| 1,767,073 A | 6/1930 | Ingold | |
| 1,863,360 A | 6/1932 | Weatherhead | |
| 1,950,947 A | 3/1934 | Mulroyan | |
| 2,023,428 A | 12/1935 | Liebhardt | |
| 2,056,524 A | 10/1936 | Johnson | |
| 2,066,473 A | 1/1937 | Jorgensen | |
| 2,097,628 A | 11/1937 | Liebhardt | |
| 2,099,335 A * | 11/1937 | Hansen | 285/308 |
| 2,108,714 A | 2/1938 | Hirsch et al. | |
| 2,116,705 A | 5/1938 | Marx et al. | |
| 2,139,745 A | 12/1938 | Goodall | |
| 2,147,355 A | 2/1939 | Scholtes | |
| 2,159,116 A | 5/1939 | Zacharias | |
| 2,211,147 A | 8/1940 | Miller | |
| 2,257,321 A | 9/1941 | Arnold | |
| 2,263,293 A | 11/1941 | Ewald | |
| 2,264,815 A | 12/1941 | Thomsen | |
| 2,340,119 A | 1/1944 | Graham | |
| 2,346,445 A | 4/1944 | Merker et al. | |
| 2,352,728 A | 7/1944 | Merker et al. | |
| 2,429,782 A | 10/1947 | Versoy | |
| 2,432,946 A | 12/1947 | Theunissen | |
| 2,470,800 A | 5/1949 | Ashton | |
| 2,479,499 A | 8/1949 | Le Clair | |
| 2,500,720 A | 3/1950 | Van der Heem | |
| 2,507,536 A | 5/1950 | Goodson | |
| 2,516,583 A | 7/1950 | Moore | |
| 2,535,740 A | 12/1950 | Knopp | |
| 2,577,009 A | 12/1951 | Frantz | |
| 2,626,974 A | 1/1953 | Howard et al. | |
| 2,630,131 A | 3/1953 | Snyder | |
| 2,661,018 A | 12/1953 | Snyder | |
| 2,701,147 A | 2/1955 | Summerville | |
| 2,722,399 A | 11/1955 | Oetiker | |
| 2,753,195 A | 7/1956 | Palmer | |
| 2,774,616 A | 12/1956 | Dodd et al. | |
| 2,790,571 A | 4/1957 | Flaith et al. | |
| 2,864,628 A | 12/1958 | Edleson | |
| 2,915,325 A * | 12/1959 | Foster | 285/319 |
| 2,926,934 A | 3/1960 | Gill | |
| 2,931,668 A | 4/1960 | Baley | |
| 2,937,892 A | 5/1960 | Prescott, Jr. | |
| 2,948,553 A | 8/1960 | Gill et al. | |
| 2,967,067 A | 1/1961 | Singer | |
| 2,991,090 A | 7/1961 | De Cenzo | |
| 3,017,203 A | 1/1962 | Macleod | |
| 3,037,497 A | 6/1962 | Roberson | |
| 3,046,028 A | 7/1962 | Nathan | |
| 3,048,415 A | 8/1962 | Shook | |
| 3,073,342 A | 1/1963 | Magorien | |
| 3,078,068 A | 2/1963 | Romney | |
| D196,473 S | 10/1963 | Hill | |
| 3,124,157 A | 3/1964 | Krzewina | |
| 3,129,020 A | 4/1964 | Bujnowski | |
| 3,171,196 A | 3/1965 | Helitas | |
| 3,191,628 A | 6/1965 | Kirkwood et al. | |
| 3,217,400 A | 11/1965 | Illesy et al. | |
| 3,217,771 A | 11/1965 | Beall et al. | |
| 3,227,380 A | 1/1966 | Pinkston | |
| 3,237,974 A | 3/1966 | Press | |
| 3,245,703 A | 4/1966 | Manly | |
| 3,276,799 A | 10/1966 | Moore et al. | |
| 3,279,497 A | 10/1966 | Norton et al. | |
| 3,314,696 A | 4/1967 | Ferguson et al. | |
| 3,317,214 A | 5/1967 | Durgom | |
| D209,166 S | 11/1967 | Hunt | |
| D209,168 S | 11/1967 | Hunt | |
| 3,352,576 A | 11/1967 | Thomas | |
| 3,382,892 A | 5/1968 | Cerbin | |
| 3,394,954 A | 7/1968 | Sarns | |
| 3,403,930 A | 10/1968 | Bernier | |
| 3,432,176 A | 3/1969 | Valenziano | |
| 3,448,760 A | 6/1969 | Cranage | |
| 3,450,424 A | 6/1969 | Calisher | |
| 3,512,808 A | 5/1970 | Graham | |
| 3,523,701 A | 8/1970 | Graham | |
| 3,538,940 A | 11/1970 | Graham | |
| 3,542,338 A | 11/1970 | Scaramucci | |
| 3,545,490 A | 12/1970 | Burrus | |
| 3,550,626 A | 12/1970 | Daniels et al. | |
| 3,560,027 A | 2/1971 | Graham | |
| 3,563,265 A | 2/1971 | Graham | |
| 3,574,314 A | 4/1971 | Quercia | |
| 3,588,149 A | 6/1971 | Demler | |
| 3,596,933 A | 8/1971 | Luckenbill | |
| 3,599,843 A | 8/1971 | Johnston | |
| 3,600,917 A | 8/1971 | Krock | |
| 3,649,050 A | 3/1972 | Woodling | |
| 3,666,297 A | 5/1972 | Marks | |
| 3,690,336 A | 9/1972 | Drum | |
| 3,712,583 A | 1/1973 | Martindale et al. | |
| 3,747,964 A | 7/1973 | Nilsen | |
| 3,750,238 A | 8/1973 | Tanner | |
| 3,815,887 A | 6/1974 | Curtis et al. | |
| 3,817,561 A | 6/1974 | Kay | |
| 3,829,135 A | 8/1974 | Forni | |
| 3,873,062 A * | 3/1975 | Johnson et al. | 285/317 |
| 3,876,234 A | 4/1975 | Harms | |
| 3,889,710 A | 6/1975 | Brost | |
| 3,899,200 A | 8/1975 | Gamble | |
| 3,921,656 A | 11/1975 | Meisenheimer, Jr. et al. | |
| 3,979,134 A | 9/1976 | Isenmann | |
| 3,990,674 A | 11/1976 | Schattenberg | |
| 3,995,659 A | 12/1976 | Cantore | |
| 4,025,049 A | 5/1977 | Schmidt | |
| 4,039,213 A | 8/1977 | Walters | |
| 4,072,330 A | 2/1978 | Brysch | |
| 4,099,748 A | 7/1978 | Kavick | |
| 4,113,627 A | 9/1978 | Leason | |
| 4,116,476 A * | 9/1978 | Porter et al. | 285/317 |
| 4,129,145 A | 12/1978 | Wynn | |
| 4,142,546 A | 3/1979 | Sandau | |
| D252,470 S | 7/1979 | Pawlak | |
| 4,181,149 A | 1/1980 | Cox | |
| 4,182,519 A | 1/1980 | Wilson | |
| D254,505 S | 3/1980 | Parsons et al. | |
| 4,200,605 A | 4/1980 | Imamura | |
| D255,145 S | 5/1980 | Nederman | |

(56) References Cited

U.S. PATENT DOCUMENTS

| | | | |
|---|---|---|---|
| 4,220,360 A | 9/1980 | Jacek et al. | |
| D258,526 S | 3/1981 | Nederman | |
| 4,253,687 A | 3/1981 | Maples | |
| D259,278 S | 5/1981 | McCaw | |
| 4,271,865 A | 6/1981 | Galloway et al. | |
| 4,282,175 A | 8/1981 | Volgstadt et al. | |
| 4,287,644 A | 9/1981 | Durand | |
| 4,290,434 A | 9/1981 | Jewett | |
| 4,294,285 A | 10/1981 | Joslyn | |
| 4,296,949 A | 10/1981 | Muetterties et al. | |
| 4,319,774 A | 3/1982 | Kavick | |
| 4,330,010 A | 5/1982 | Drescher et al. | |
| 4,330,142 A | 5/1982 | Paini | |
| 4,331,175 A | 5/1982 | Brake et al. | |
| 4,331,177 A * | 5/1982 | Makishima | 285/308 |
| 4,340,200 A | 7/1982 | Stegmeier | |
| 4,345,786 A | 8/1982 | Egert | |
| 4,346,703 A | 8/1982 | Dennehey | |
| 4,351,351 A | 9/1982 | Flory et al. | |
| 4,366,816 A | 1/1983 | Bayard et al. | |
| 4,393,548 A | 7/1983 | Herb | |
| 4,397,442 A | 8/1983 | Larkin | |
| 4,407,526 A | 10/1983 | Cicenas | |
| 4,431,031 A | 2/1984 | Ettlinger | |
| 4,431,218 A | 2/1984 | Paul | |
| 4,434,121 A | 2/1984 | Schaper | |
| 4,436,125 A | 3/1984 | Blenkush | |
| 4,437,689 A | 3/1984 | Goebel et al. | |
| 4,439,188 A | 3/1984 | Dennehey | |
| 4,458,719 A | 7/1984 | Strybel | |
| 4,489,914 A | 12/1984 | Stevenson et al. | |
| 4,489,961 A | 12/1984 | Laidig | |
| 4,500,118 A | 2/1985 | Blenkush | |
| 4,501,280 A | 2/1985 | Hood | |
| 4,527,745 A | 7/1985 | Butterfield et al. | |
| 4,541,457 A | 9/1985 | Blenkush | |
| 4,541,657 A | 9/1985 | Smyth | |
| 4,553,587 A | 11/1985 | Traylor | |
| D282,962 S | 3/1986 | Gerber | |
| 4,576,359 A * | 3/1986 | Oetiker | 285/317 |
| 4,580,816 A | 4/1986 | Campbell et al. | |
| 4,603,888 A | 8/1986 | Goodall et al. | |
| 4,603,890 A | 8/1986 | Huppee | |
| 4,613,112 A | 9/1986 | Phlipot et al. | |
| 4,616,859 A | 10/1986 | Brunet | |
| 4,626,001 A | 12/1986 | Lee | |
| 4,630,847 A | 12/1986 | Blenkush | |
| 4,632,436 A | 12/1986 | Kimura | |
| 4,635,972 A | 1/1987 | Lyall | |
| 4,645,245 A | 2/1987 | Cunningham | |
| 4,658,326 A | 4/1987 | Clark et al. | |
| 4,659,116 A | 4/1987 | Cameron | |
| 4,694,544 A | 9/1987 | Chapman | |
| 4,698,027 A | 10/1987 | Vandame | |
| 4,699,298 A | 10/1987 | Grant et al. | |
| 4,700,926 A | 10/1987 | Hansen | |
| 4,703,957 A | 11/1987 | Blenkush | |
| 4,706,847 A | 11/1987 | Sankey et al. | |
| 4,712,280 A | 12/1987 | Fildan | |
| 4,733,890 A | 3/1988 | Vyse | |
| 4,738,401 A | 4/1988 | Filicicchia | |
| 4,753,268 A * | 6/1988 | Palau | 285/317 |
| 4,768,558 A | 9/1988 | Weber | |
| 4,776,067 A | 10/1988 | Sorensen | |
| 4,790,567 A | 12/1988 | Kawano et al. | |
| 4,790,569 A | 12/1988 | Chaffee | |
| 4,792,115 A | 12/1988 | Jindra et al. | |
| 4,793,637 A | 12/1988 | Laipply et al. | |
| 4,806,123 A | 2/1989 | Konishi et al. | |
| D300,361 S | 3/1989 | Tokarz | |
| 4,824,148 A | 4/1989 | Grabowski | |
| 4,827,921 A | 5/1989 | Rugheimer | |
| 4,832,237 A | 5/1989 | Hurford, Jr. | |
| 4,834,423 A | 5/1989 | DeLand | |
| 4,844,512 A | 7/1989 | Gahwiler | |
| 4,863,201 A | 9/1989 | Carstens | |
| 4,863,202 A | 9/1989 | Oldford | |
| 4,896,402 A | 1/1990 | Jansen et al. | |
| 4,900,065 A | 2/1990 | Houck | |
| 4,903,995 A | 2/1990 | Blenkush et al. | |
| 4,923,228 A | 5/1990 | Laipply et al. | |
| 4,928,859 A | 5/1990 | Krahn et al. | |
| 4,928,999 A | 5/1990 | Landriault et al. | |
| 4,934,655 A * | 6/1990 | Blenkush et al. | 285/308 |
| 4,935,992 A | 6/1990 | Due | |
| 4,946,200 A | 8/1990 | Blenkush et al. | |
| 4,946,204 A | 8/1990 | Boticki | |
| 4,949,745 A | 8/1990 | McKeon | |
| 4,966,398 A | 10/1990 | Peterson | |
| 4,969,879 A | 11/1990 | Lichte | |
| D313,067 S | 12/1990 | Kotake et al. | |
| D313,277 S | 12/1990 | Haining | |
| D314,050 S | 1/1991 | Sone | |
| D314,233 S | 1/1991 | Medvick | |
| 4,982,736 A * | 1/1991 | Schneider | 285/319 |
| 4,991,880 A | 2/1991 | Bernart | |
| 5,009,252 A | 4/1991 | Faughn | |
| 5,015,014 A | 5/1991 | Sweeney | |
| 5,029,908 A | 7/1991 | Belisaire | |
| 5,033,777 A * | 7/1991 | Blenkush | 285/317 |
| D319,312 S | 8/1991 | Schneider | |
| 5,052,725 A * | 10/1991 | Meyer et al. | 285/308 |
| 5,074,601 A | 12/1991 | Spors et al. | |
| 5,076,615 A | 12/1991 | Sampson | |
| 5,078,429 A | 1/1992 | Braut et al. | |
| 5,085,472 A | 2/1992 | Guest | |
| 5,090,448 A | 2/1992 | Truchet | |
| 5,090,747 A * | 2/1992 | Kotake | 285/317 |
| 5,094,482 A | 3/1992 | Petty et al. | |
| 5,104,158 A * | 4/1992 | Meyer et al. | 285/308 |
| 5,106,127 A | 4/1992 | Briet | |
| D326,155 S | 5/1992 | Boehringer et al. | |
| 5,110,163 A | 5/1992 | Benson et al. | |
| 5,112,084 A | 5/1992 | Washizu | |
| 5,114,250 A | 5/1992 | Usui | |
| D326,715 S | 6/1992 | Schmidt | |
| 5,123,677 A | 6/1992 | Kreczko et al. | |
| 5,143,381 A | 9/1992 | Temple | |
| 5,160,177 A | 11/1992 | Washizu | |
| 5,160,474 A | 11/1992 | Huff | |
| 5,165,733 A | 11/1992 | Sampson | |
| 5,169,161 A | 12/1992 | Jones | |
| D332,482 S | 1/1993 | Petty et al. | |
| 5,176,406 A | 1/1993 | Straghan | |
| 5,178,303 A | 1/1993 | Blenkush et al. | |
| 5,181,752 A | 1/1993 | Benson et al. | |
| D333,178 S | 2/1993 | Novy | |
| 5,190,224 A | 3/1993 | Hamilton | |
| 5,201,552 A * | 4/1993 | Hohmann et al. | 285/308 |
| 5,219,185 A * | 6/1993 | Oddenino | 285/317 |
| 5,222,279 A | 6/1993 | Frano et al. | |
| 5,228,724 A | 7/1993 | Godeau | |
| 5,232,020 A | 8/1993 | Mason et al. | |
| D339,417 S | 9/1993 | Sampson et al. | |
| 5,251,025 A | 10/1993 | Cooper et al. | |
| 5,273,053 A | 12/1993 | Pohndorf | |
| 5,297,820 A | 3/1994 | Martin | |
| 5,297,826 A | 3/1994 | Percebois et al. | |
| 5,316,041 A | 5/1994 | Ramacier, Jr. et al. | |
| 5,318,332 A | 6/1994 | Hohmann et al. | |
| 5,330,235 A | 7/1994 | Wagner et al. | |
| 5,348,051 A | 9/1994 | Kallenbach | |
| 5,348,354 A | 9/1994 | Badoureaux | |
| 5,353,836 A | 10/1994 | deCler et al. | |
| 5,356,183 A | 10/1994 | Cole | |
| 5,374,088 A | 12/1994 | Moretti et al. | |
| 5,385,311 A | 1/1995 | Morikawa et al. | |
| 5,385,331 A | 1/1995 | Allread et al. | |
| D357,307 S | 4/1995 | Ramacier, Jr. et al. | |
| 5,405,333 A | 4/1995 | Richmond | |
| 5,405,339 A | 4/1995 | Kohnen et al. | |
| 5,405,340 A | 4/1995 | Fageol et al. | |
| 5,411,300 A | 5/1995 | Mitsui | |
| 5,417,442 A | 5/1995 | Jornhagen | |

(56) References Cited

U.S. PATENT DOCUMENTS

| | | |
|---|---|---|
| 5,421,622 A | 6/1995 | Godeau |
| 5,437,650 A | 8/1995 | Larkin et al. |
| 5,440,792 A | 8/1995 | Ida |
| 5,462,313 A | 10/1995 | Rea et al. |
| 5,494,074 A | 2/1996 | Ramacier, Jr. et al. |
| D369,409 S | 4/1996 | Salter |
| 5,507,733 A | 4/1996 | Larkin et al. |
| 5,511,527 A | 4/1996 | Lorraine et al. |
| D372,093 S | 7/1996 | Sampson et al. |
| 5,536,258 A | 7/1996 | Folden |
| 5,542,712 A | 8/1996 | Klinger et al. |
| 5,547,166 A | 8/1996 | Engdahl |
| 5,547,230 A | 8/1996 | Bank et al. |
| 5,553,895 A | 9/1996 | Karl et al. |
| D375,160 S | 10/1996 | Sampson et al. |
| 5,568,946 A | 10/1996 | Jackowski |
| 5,595,217 A | 1/1997 | Gillen et al. |
| 5,601,317 A | 2/1997 | Crouse et al. |
| 5,607,087 A * | 3/1997 | Wery et al. ............ 285/317 |
| 5,607,190 A | 3/1997 | Exandier et al. |
| 5,617,609 A | 4/1997 | Bently |
| 5,620,025 A | 4/1997 | Lewin |
| 5,628,726 A | 5/1997 | Cotter |
| D380,262 S | 6/1997 | Van Funderburk et al. |
| 5,639,064 A | 6/1997 | deCler et al. |
| D382,639 S | 8/1997 | Musgrave et al. |
| D384,731 S | 10/1997 | Ramacier, Jr. et al. |
| 5,681,062 A | 10/1997 | Fukao et al. |
| 5,682,662 A | 11/1997 | Coules et al. |
| 5,683,117 A | 11/1997 | Corbett et al. |
| D387,147 S | 12/1997 | Vandermast et al. |
| 5,692,783 A | 12/1997 | Watanabe et al. |
| 5,695,223 A | 12/1997 | Boticki |
| D388,876 S | 1/1998 | Sampson |
| 5,709,244 A | 1/1998 | Patriquin et al. |
| 5,725,258 A | 3/1998 | Kujawski |
| 5,737,810 A | 4/1998 | Krauss |
| 5,745,957 A | 5/1998 | Khokhar et al. |
| 5,746,414 A | 5/1998 | Weldon et al. |
| 5,762,646 A | 6/1998 | Cotter |
| 5,784,750 A | 7/1998 | Sankovic et al. |
| 5,799,987 A | 9/1998 | Sampson |
| 5,820,614 A | 10/1998 | Erskine et al. |
| 5,837,180 A | 11/1998 | Linder et al. |
| 5,845,943 A | 12/1998 | Ramacier, Jr. et al. |
| 5,855,568 A | 1/1999 | Battiato et al. |
| 5,879,033 A | 3/1999 | Hansel et al. |
| 5,882,047 A | 3/1999 | Ostrander et al. |
| 5,884,531 A | 3/1999 | Koenig |
| D407,803 S | 4/1999 | Redman |
| 5,897,142 A | 4/1999 | Kulevsky |
| 5,911,367 A | 6/1999 | McInerney |
| 5,911,403 A | 6/1999 | deCler et al. |
| 5,911,404 A | 6/1999 | Cheng |
| 5,930,424 A | 7/1999 | Heimberger et al. |
| 5,937,501 A | 8/1999 | Imgram |
| 5,938,244 A | 8/1999 | Meyer |
| 5,941,577 A * | 8/1999 | Musellec ............ 285/317 |
| 5,942,730 A | 8/1999 | Schwarz et al. |
| D413,967 S | 9/1999 | Yuen |
| 5,957,898 A | 9/1999 | Jepson et al. |
| 5,961,157 A | 10/1999 | Baron et al. |
| 5,964,485 A | 10/1999 | Hame et al. |
| 5,965,077 A | 10/1999 | Rowley et al. |
| 5,975,489 A | 11/1999 | deCler et al. |
| 5,984,378 A | 11/1999 | Ostrander et al. |
| 5,988,704 A | 11/1999 | Ryhman |
| 6,012,743 A | 1/2000 | Godeau et al. |
| 6,015,171 A | 1/2000 | Schorn |
| D419,861 S | 2/2000 | Khokhar |
| 6,019,348 A | 2/2000 | Powell |
| 6,024,124 A | 2/2000 | Braun et al. |
| 6,029,701 A | 2/2000 | Chaffardon et al. |
| 6,032,691 A | 3/2000 | Powell et al. |
| 6,041,805 A | 3/2000 | Gydesen et al. |
| D422,487 S | 4/2000 | Khokhar |
| 6,050,297 A | 4/2000 | Ostrowski et al. |
| 6,076,234 A | 6/2000 | Khokhar et al. |
| 6,077,245 A | 6/2000 | Heinrich et al. |
| 6,077,259 A | 6/2000 | Caizza et al. |
| 6,082,401 A | 7/2000 | Braun et al. |
| 6,086,044 A | 7/2000 | Guest |
| 6,089,540 A | 7/2000 | Heinrichs et al. |
| 6,095,983 A | 8/2000 | Wawro |
| 6,099,045 A | 8/2000 | Pirona |
| 6,112,855 A | 9/2000 | Camacho et al. |
| 6,123,690 A | 9/2000 | Mejslov |
| 6,129,390 A * | 10/2000 | Ohlsson ............ 285/317 |
| 6,135,150 A | 10/2000 | Powell et al. |
| 6,135,992 A | 10/2000 | Wang |
| 6,142,538 A | 11/2000 | Volgstadt et al. |
| 6,145,896 A | 11/2000 | Vitel et al. |
| 6,152,914 A | 11/2000 | Van De Kerkhof et al. |
| 6,155,610 A | 12/2000 | Godeau et al. |
| 6,161,578 A | 12/2000 | Braun et al. |
| 6,176,523 B1 | 1/2001 | Winslett |
| 6,182,694 B1 | 2/2001 | Sievers et al. |
| 6,189,560 B1 | 2/2001 | Reynolds |
| 6,199,915 B1 | 3/2001 | Becker |
| 6,199,919 B1 | 3/2001 | Kawasaki et al. |
| 6,199,920 B1 | 3/2001 | Neustadtl |
| 6,206,028 B1 | 3/2001 | Holden et al. |
| 6,221,064 B1 | 4/2001 | Nadal |
| 6,231,089 B1 * | 5/2001 | DeCler et al. ............ 285/308 |
| D444,054 S | 6/2001 | Bernard et al. |
| 6,250,688 B1 | 6/2001 | Kirby |
| 6,257,626 B1 | 7/2001 | Campau |
| 6,260,851 B1 | 7/2001 | Baron |
| 6,261,282 B1 | 7/2001 | Jepson et al. |
| 6,293,596 B1 | 9/2001 | Kinder |
| 6,296,508 B1 | 10/2001 | Kuwahara et al. |
| 6,296,796 B1 | 10/2001 | Gordon |
| 6,302,147 B1 | 10/2001 | Rose et al. |
| 6,318,764 B1 | 11/2001 | Trede et al. |
| 6,344,033 B1 | 2/2002 | Jepson et al. |
| 6,382,593 B1 | 5/2002 | deCler et al. |
| D459,206 S | 6/2002 | Caveney et al. |
| 6,402,207 B1 | 6/2002 | Segal et al. |
| 6,422,574 B1 | 7/2002 | Mooklar |
| 6,423,053 B1 | 7/2002 | Lee |
| 6,439,620 B1 | 8/2002 | Guest |
| 6,454,314 B1 | 9/2002 | Grosspietsch et al. |
| 6,481,758 B1 | 11/2002 | Andre et al. |
| 6,481,759 B1 | 11/2002 | Kawasaki et al. |
| 6,485,064 B1 | 11/2002 | Davidson |
| 6,485,483 B1 | 11/2002 | Fujii |
| 6,497,433 B1 | 12/2002 | Ketcham |
| 6,505,866 B1 | 1/2003 | Nakamura et al. |
| 6,508,807 B1 | 1/2003 | Peters |
| 6,520,546 B2 | 2/2003 | Szabo |
| D471,261 S | 3/2003 | Kozu |
| 6,540,263 B1 | 4/2003 | Sausner |
| 6,543,745 B1 | 4/2003 | Enerson |
| 6,595,964 B2 | 7/2003 | Finley et al. |
| 6,609,696 B2 | 8/2003 | Enerson |
| 6,612,634 B1 | 9/2003 | Zoppas |
| 6,626,419 B2 | 9/2003 | DeCler et al. |
| 6,626,465 B2 * | 9/2003 | Lacroix et al. ............ 285/317 |
| D481,125 S | 10/2003 | Hayamizu |
| 6,641,177 B1 | 11/2003 | Pinciaro |
| 6,649,829 B2 | 11/2003 | Garber et al. |
| 6,652,007 B1 | 11/2003 | Hwang |
| D484,241 S | 12/2003 | Peters et al. |
| 6,669,681 B2 | 12/2003 | Jepson et al. |
| 6,676,172 B2 | 1/2004 | Alksnis |
| 6,682,547 B2 | 1/2004 | McEwen |
| D486,909 S | 2/2004 | Cise et al. |
| 6,688,654 B2 | 2/2004 | Romero |
| 6,692,038 B2 | 2/2004 | Braun |
| 6,695,817 B1 | 2/2004 | Fangrow |
| 6,705,591 B2 | 3/2004 | deCler |
| 6,722,705 B2 | 4/2004 | Korkor |
| 6,722,708 B2 | 4/2004 | Morohoshi et al. |
| 6,762,365 B2 | 7/2004 | Inoue et al. |

(56) References Cited

U.S. PATENT DOCUMENTS

| | | |
|---|---|---|
| 6,767,017 B2 | 7/2004 | Crapart et al. |
| D495,050 S | 8/2004 | Guala |
| 6,783,520 B1 | 8/2004 | Candray et al. |
| D497,428 S | 10/2004 | Hayamizu |
| 6,799,747 B1 | 10/2004 | Lai |
| D498,533 S | 11/2004 | Hayamizu |
| 6,814,726 B1 | 11/2004 | Lauer |
| 6,840,277 B1 | 1/2005 | Nimberger |
| 6,846,021 B2 | 1/2005 | Rohde et al. |
| 6,848,602 B2 | 2/2005 | deCler et al. |
| 6,848,723 B2 | 2/2005 | Lamich |
| 6,863,314 B2 | 3/2005 | Guest |
| 6,871,669 B2 | 3/2005 | Meyer et al. |
| 6,871,878 B2 | 3/2005 | Miros |
| D503,778 S | 4/2005 | Wicks |
| 6,886,803 B2 | 5/2005 | Mikiya et al. |
| 6,897,374 B2 | 5/2005 | Garber et al. |
| 6,899,315 B2 | 5/2005 | Maiville et al. |
| 6,902,144 B2 | 6/2005 | deCler |
| D507,647 S | 7/2005 | Beck et al. |
| 6,916,007 B2 | 7/2005 | deCler et al. |
| 6,916,050 B2 | 7/2005 | Milhas |
| 6,926,311 B2 * | 8/2005 | Chang et al. ............ 285/317 |
| 6,929,246 B2 | 8/2005 | Arzenton et al. |
| 6,945,273 B2 | 9/2005 | Reid |
| 6,949,084 B2 | 9/2005 | Marggi et al. |
| 6,962,275 B2 | 11/2005 | deCler et al. |
| 6,978,800 B2 | 12/2005 | deCler et al. |
| 6,981,547 B2 | 1/2006 | Maguire et al. |
| 6,997,486 B2 | 2/2006 | Milhas |
| 6,997,919 B2 | 2/2006 | Olsen et al. |
| 7,005,581 B2 | 2/2006 | Burnette |
| 7,011,342 B2 | 3/2006 | Guivarc'h et al. |
| 7,014,214 B2 | 3/2006 | Kaneko |
| D522,109 S | 5/2006 | White et al. |
| 7,040,670 B2 | 5/2006 | Madden |
| 7,044,161 B2 | 5/2006 | Tiberghien |
| 7,044,506 B2 | 5/2006 | Dong |
| D523,553 S | 6/2006 | Beck et al. |
| 7,080,665 B2 | 7/2006 | Whall |
| 7,081,223 B2 | 7/2006 | Khoury |
| 7,108,297 B2 | 9/2006 | Takayanagi et al. |
| 7,118,138 B1 | 10/2006 | Rowley et al. |
| 7,128,348 B2 | 10/2006 | Kawamura et al. |
| 7,137,654 B2 | 11/2006 | Segal et al. |
| 7,140,592 B2 | 11/2006 | Phillips |
| 7,147,252 B2 | 12/2006 | Teuscher et al. |
| 7,150,478 B2 | 12/2006 | Poirier et al. |
| 7,153,296 B2 | 12/2006 | Mitchell |
| 7,163,022 B2 | 1/2007 | Whall |
| D540,944 S | 4/2007 | Guala |
| 7,210,917 B2 | 5/2007 | Lai et al. |
| D547,446 S | 7/2007 | Racz et al. |
| D550,355 S | 9/2007 | Racz et al. |
| D557,409 S | 12/2007 | Veliss et al. |
| 7,316,428 B2 | 1/2008 | Takayanagi et al. |
| D564,660 S | 3/2008 | Hayashi |
| 7,343,931 B2 | 3/2008 | Packham |
| D567,340 S | 4/2008 | Tiberghien |
| 7,352,771 B2 | 4/2008 | Garber |
| D569,507 S | 5/2008 | Blanchard |
| D569,955 S | 5/2008 | Chen |
| 7,377,553 B2 | 5/2008 | Takayanagi |
| D570,457 S | 6/2008 | Brown |
| 7,390,029 B2 | 6/2008 | Matsubara |
| 7,394,375 B2 | 7/2008 | Johnson |
| 7,434,842 B2 | 10/2008 | Schmidt |
| 7,434,846 B2 | 10/2008 | Baumgartner |
| 7,448,653 B2 * | 11/2008 | Jensen et al. ............ 285/308 |
| 7,464,970 B2 | 12/2008 | Yamada et al. |
| 7,467,813 B2 | 12/2008 | Gunderson |
| 7,469,472 B2 | 12/2008 | DeCler et al. |
| 7,478,840 B2 | 1/2009 | Youssefifar |
| 7,488,446 B2 | 2/2009 | Meyer et al. |
| 7,494,156 B2 | 2/2009 | Okada |
| 7,503,595 B2 | 3/2009 | McKay |
| 7,516,990 B2 | 4/2009 | Jamison et al. |
| 7,546,857 B2 | 6/2009 | Chadbourne et al. |
| 7,547,047 B2 | 6/2009 | deCler et al. |
| D595,845 S | 7/2009 | Miros et al. |
| D595,846 S | 7/2009 | Racz et al. |
| D596,288 S | 7/2009 | Racz et al. |
| D596,739 S | 7/2009 | Ng et al. |
| 7,562,906 B2 | 7/2009 | Schmidt |
| 7,566,077 B2 | 7/2009 | Tsurumi |
| 7,581,763 B2 | 9/2009 | Salomon-Bahls |
| D602,128 S | 10/2009 | Williams et al. |
| 7,614,666 B2 | 11/2009 | Eggert et al. |
| 7,631,660 B2 | 12/2009 | deCler et al. |
| 7,647,954 B2 | 1/2010 | Garber et al. |
| 7,666,178 B2 | 2/2010 | McMichael |
| D612,019 S | 3/2010 | Williams et al. |
| D612,021 S | 3/2010 | Schmidt |
| 7,677,608 B2 | 3/2010 | Takayanagi |
| D613,853 S | 4/2010 | Ng et al. |
| 7,695,020 B2 | 4/2010 | Schmidt |
| 7,708,025 B2 | 5/2010 | Johnson |
| 7,731,244 B2 * | 6/2010 | Miros et al. ............ 285/317 |
| D619,706 S | 7/2010 | Schon et al. |
| 7,753,415 B2 * | 7/2010 | Tiberghien et al. ............ 285/308 |
| 7,770,939 B2 * | 8/2010 | Jensen et al. ............ 285/308 |
| 7,806,139 B2 | 10/2010 | Packham et al. |
| 7,841,357 B2 | 11/2010 | Rankin |
| D629,894 S | 12/2010 | Lombardi, III et al. |
| 7,849,877 B2 | 12/2010 | Tan et al. |
| D630,320 S | 1/2011 | Lombardi, III et al. |
| D632,783 S | 2/2011 | Maesarapu |
| 7,878,553 B2 | 2/2011 | Wicks et al. |
| D634,840 S | 3/2011 | Lombardi, III et al. |
| D639,398 S | 6/2011 | Wilhelm |
| 7,954,374 B2 | 6/2011 | Rankin |
| 7,954,515 B2 | 6/2011 | Gerst |
| D642,244 S | 7/2011 | Wilhelm |
| 7,976,071 B2 | 7/2011 | Bibby |
| D645,547 S | 9/2011 | Lombardi, III et al. |
| D649,240 S | 11/2011 | Lewis et al. |
| D650,478 S | 12/2011 | Lewis |
| D652,510 S | 1/2012 | Lombardi, III et al. |
| D652,511 S | 1/2012 | Lombardi, III et al. |
| D654,573 S | 2/2012 | Lombardi, III et al. |
| 8,113,546 B2 * | 2/2012 | Jensen et al. ............ 285/308 |
| D655,393 S | 3/2012 | Whitaker |
| D663,022 S | 7/2012 | Lombardi, III et al. |
| 8,235,426 B2 | 8/2012 | Pisula, Jr. et al. |
| 8,397,758 B2 | 3/2013 | Packham |
| 2001/0017466 A1 | 8/2001 | Braun |
| 2002/0022762 A1 | 2/2002 | Beane et al. |
| 2002/0093192 A1 | 7/2002 | Matkovich |
| 2002/0140172 A1 | 10/2002 | Platusich |
| 2002/0156344 A1 | 10/2002 | Pasricha et al. |
| 2002/0185861 A1 | 12/2002 | Inoue |
| 2003/0004397 A1 | 1/2003 | Kameya et al. |
| 2003/0067162 A1 | 4/2003 | Welsh et al. |
| 2003/0193188 A1 | 10/2003 | Miros |
| 2003/0230894 A1 | 12/2003 | Cleveland et al. |
| 2004/0021318 A1 | 2/2004 | Fritze et al. |
| 2004/0056484 A1 | 3/2004 | Kwon et al. |
| 2004/0094903 A1 | 5/2004 | Sutherland |
| 2004/0195830 A1 | 10/2004 | Gilmour |
| 2004/0199143 A1 | 10/2004 | Lauer |
| 2004/0227346 A1 | 11/2004 | Jamison et al. |
| 2004/0232696 A1 | 11/2004 | Andre |
| 2005/0033237 A1 | 2/2005 | Fentress et al. |
| 2005/0046184 A1 | 3/2005 | Chang |
| 2005/0056121 A1 | 3/2005 | Lyman |
| 2005/0057042 A1 | 3/2005 | Wicks |
| 2005/0082828 A1 | 4/2005 | Wicks et al. |
| 2005/0087981 A1 | 4/2005 | Yamada et al. |
| 2005/0209583 A1 | 9/2005 | Powers et al. |
| 2005/0217265 A1 | 10/2005 | Popp et al. |
| 2005/0242579 A1 | 11/2005 | Bright et al. |
| 2005/0275220 A1 | 12/2005 | Shu |
| 2006/0066100 A1 | 3/2006 | Nakashima et al. |
| 2006/0128180 A1 | 6/2006 | Gammons |

(56) References Cited

U.S. PATENT DOCUMENTS

| | | | |
|---|---|---|---|
| 2006/0152003 | A1 | 7/2006 | Slunick et al. |
| 2006/0202146 | A1 | 9/2006 | Doyle |
| 2006/0264814 | A1 | 11/2006 | Sage |
| 2006/0293629 | A1 | 12/2006 | Cote, Sr. et al. |
| 2007/0025811 | A1 | 2/2007 | Wilhelm |
| 2007/0029795 | A1 | 2/2007 | Moner et al. |
| 2007/0029796 | A1 | 2/2007 | Bibby |
| 2007/0106213 | A1 | 5/2007 | Spera et al. |
| 2007/0137718 | A1 | 6/2007 | Rushlander et al. |
| 2007/0169825 | A1 | 7/2007 | Packham et al. |
| 2007/0209716 | A1 | 9/2007 | Rankin |
| 2007/0284875 | A1 | 12/2007 | Salomon-Bahls et al. |
| 2008/0007051 | A1 | 1/2008 | Jensen et al. |
| 2008/0011703 | A1 | 1/2008 | Schmeisser et al. |
| 2008/0012314 | A1 | 1/2008 | Harger et al. |
| 2008/0018105 | A1 | 1/2008 | Le Bars |
| 2008/0048448 | A1 | 2/2008 | Jamison et al. |
| 2008/0078464 | A1 | 4/2008 | Loewe |
| 2008/0111371 | A1 | 5/2008 | Feger et al. |
| 2008/0111372 | A1 | 5/2008 | Trede et al. |
| 2008/0129047 | A1 | 6/2008 | Blivet et al. |
| 2008/0164694 | A1 | 7/2008 | Zdroik et al. |
| 2008/0191466 | A1 | 8/2008 | Knipple et al. |
| 2008/0200901 | A1 | 8/2008 | Rasmussen et al. |
| 2008/0277923 | A1 | 11/2008 | Brandt et al. |
| 2008/0277924 | A1 | 11/2008 | Jensen et al. |
| 2008/0284167 | A1 | 11/2008 | Lim et al. |
| 2008/0287920 | A1 | 11/2008 | Fangrow et al. |
| 2009/0079187 | A1 | 3/2009 | Malone |
| 2009/0127847 | A1 | 5/2009 | Hagen et al. |
| 2009/0129047 | A1 | 5/2009 | Park et al. |
| 2009/0140519 | A1 | 6/2009 | Pavnaskar et al. |
| 2009/0167018 | A1* | 7/2009 | Lien .............................. 285/308 |
| 2009/0187166 | A1 | 7/2009 | Young |
| 2009/0188575 | A1 | 7/2009 | Williams et al. |
| 2009/0256355 | A1 | 10/2009 | Wicks et al. |
| 2010/0001516 | A1 | 1/2010 | Pisula, Jr. et al. |
| 2010/0056975 | A1 | 3/2010 | Dale et al. |
| 2010/0078934 | A1 | 4/2010 | Matsunaga |
| 2010/0185040 | A1 | 7/2010 | Uber et al. |
| 2010/0194100 | A1 | 8/2010 | Koch |
| 2010/0276922 | A1 | 11/2010 | Rehder et al. |
| 2010/0295295 | A1 | 11/2010 | Schmidt |
| 2010/0301599 | A1 | 12/2010 | Jensen et al. |
| 2010/0319796 | A1 | 12/2010 | Whitaker |
| 2011/0012340 | A1 | 1/2011 | Packham et al. |
| 2011/0127767 | A1 | 6/2011 | Wicks et al. |
| 2011/0204621 | A1 | 8/2011 | Whitaker et al. |
| 2011/0204622 | A1 | 8/2011 | Lewis et al. |
| 2011/0210541 | A1* | 9/2011 | Lewis et al. ................... 285/317 |
| 2012/0031515 | A1 | 2/2012 | Whitaker |
| 2012/0068457 | A1 | 3/2012 | Pisula, Jr. et al. |
| 2012/0299290 | A1 | 11/2012 | Pisula, Jr. et al. |
| 2012/0299296 | A1 | 11/2012 | Lombardi, III |

FOREIGN PATENT DOCUMENTS

| | | |
|---|---|---|
| DE | 3439522 | 8/1985 |
| DE | 3533000 | 3/1987 |
| DE | 4122455 | 1/1993 |
| DE | 4138064 C1 | 5/1993 |
| DE | 19800050 | 7/1998 |
| DE | 102005015343 | 10/2006 |
| EP | 0360634 | 3/1990 |
| EP | 0390746 | 10/1990 |
| EP | 0267067 | 7/1991 |
| EP | 0482277 | 4/1992 |
| EP | 0592823 | 4/1994 |
| EP | 0715111 | 6/1996 |
| EP | 0865779 | 9/1998 |
| EP | 0877891 | 11/1998 |
| EP | 0890054 | 1/1999 |
| EP | 0982525 | 3/2000 |
| EP | 1497582 | 1/2005 |
| EP | 1564469 | 8/2005 |
| EP | 1843074 | 10/2007 |
| FR | 2031965 | 11/1970 |
| FR | 2429370 | 1/1980 |
| FR | 280871 | 10/2001 |
| FR | 2853043 | 10/2004 |
| FR | 2870921 | 12/2005 |
| FR | 2903164 | 1/2008 |
| GB | 583459 | 12/1946 |
| GB | 890775 | 3/1962 |
| GB | 2177769 | 1/1987 |
| GB | 2218166 | 11/1989 |
| GB | 2271157 | 4/1994 |
| GB | 2379253 | 3/2003 |
| JP | 53-006918 | 1/1978 |
| JP | 5-223189 | 8/1993 |
| JP | 7-145889 | 6/1995 |
| JP | 10-169869 | 6/1998 |
| JP | 11-82849 | 3/1999 |
| JP | 2003-42363 | 2/2003 |
| JP | 2003-42368 | 2/2003 |
| JP | 6-512540 | 4/2006 |
| WO | WO 93/17270 | 9/1993 |
| WO | WO 95/08732 | 3/1995 |
| WO | WO 00/79172 | 12/2000 |
| WO | WO 2004/027269 | 4/2004 |
| WO | WO 2004/104466 | 12/2004 |
| WO | WO 2005/064216 | 7/2005 |
| WO | WO 2006/031958 | 3/2006 |
| WO | WO 2006/073778 | 7/2006 |
| WO | WO 2006/084171 | 8/2006 |
| WO | 2006135666 A2 | 12/2006 |
| WO | WO 2006/135666 | 12/2006 |
| WO | WO 2007/038222 | 4/2007 |
| WO | WO 2007/116387 | 10/2007 |
| WO | WO 2007/120620 | 10/2007 |
| WO | WO 2008/023021 | 2/2008 |
| WO | WO 2009/026441 | 2/2009 |

OTHER PUBLICATIONS

About Us [online], Thuro Metal Products [retrieved on Apr. 9, 2010], retrieved from the Internet: <URL: http://www.thurometal.com/about.html>, 2 pages.

Barbed Tee Adapter, 1/2 in to 2/8 in to 1/2 in [Item # F1728], http://www.horticulturesource.com/product_info.php/products_id/4016/language/en; dated accessed Sep. 14, 2009, 3 pages.

Brochure, "Precision Components", Value Plastics, Inc., 2002, 132 pages.

Capabilities [online], Jay Manufacturing Corp., retrieved on Apr. 9, 2010, retrieved from the Internet: <URL: http://www.jaymfg.com/capabilities.htm>, 2 pages.

Flojet "Quick Connect" Port System Adapter 90 Elbow Type Quad Port X 1/2" Hose Barb, http://www.amazon.com/Quick-Connect-Port-System-Quad-Barb-90/dp/B0000AZ771/ref=sr_1_16?s=sporting-goods&ie=UTF8&qid=1300220596&sr=1-16, date accessed Sep. 14, 2009; 3 pages.

High-Flow Quick Disconnect Couplings; http://www.coleparmer.com/catalog/product_view.asp?sku=3130355; date accessed Sep. 14, 2009, 3 pages.

Mills, The Process of Vacuum-forming Plastic Parts, IPFrontline.com [online], retrieved on Apr. 9, 2010, retrieved from the Internet: <URL: http://www.ipfrontline.com/depts/article.asp?id=453&deptid=2>, 3 pages.

Nylon, Polypropylene Kynar (PVDF) Plastic Fittings for Flexible Tubing & Hose, http://www.omega.com/pdf/tubing/fittings_tubing_hose/nylon_poly_kynar/nylon.asp; dated accessed Sep. 14, 2009, 2 pages.

Science of Hose Barbs, Colder Products Company, http://www.pddnet.com/article-the-science-of-hose-barbs/, date accessed Sep. 4, 2009, 6 pages.

Stackable Hose Barb Elbow—1/2" CTS x 1/2 ID Barb, http://www.freshwatersystems.com/p-1714-stackable-hose-barb-elbow-12-cts-x-12-id-barb.aspx?affiliatied=10052&utm_source=shopzilla&utm_medium=Feed&utm_campaign=Product&utm_term=3512-1008, date accessed Sep. 14, 2009, 1 page.

(56) References Cited

OTHER PUBLICATIONS

Stainless Steel Overview: History [online], Stainless Steel Industry of North America, retrieved on Apr. 9, 2010, retrieved from the Internet: <URL: http://www.ssina.com/overview/history.html>, 1 page.

International Search Report and Written Opinion dated May 23, 2011, PCT/US2010/061896, 11 pages.

Japanese Office Action dated Jul. 9, 2014 for International Application No. 2012-546210, 13 pages.

EP Search Report mailed Jul. 25, 2014 for Application No. 10803324.2-1662, 5 pages.

Japanese Patent Office, "Decision of Refusal dated Jul. 15, 2015", Japanese Patent Application No. 2012-546210, 6 pages.

Singapore Office Action dated Oct. 16, 2014, Application No. 2014/350822389P, 11 pages.

Chinese State Intellectual Property Office (SIPO); Office Action dated May 14, 2015; Chinese Patent Application No. 201080063938.8; 11 pages.

* cited by examiner

MALE BAYONET CONNECTOR

CROSS REFERENCE TO RELATED APPLICATIONS

This application claims the benefit of priority pursuant to 35 U.S.C. §119(e) of U.S. provisional application No. 61/289,545 filed 23 Dec. 2009 entitled "Male bayonet connector," which is hereby incorporated herein by reference in its entirety. This application is a continuation-in-part of U.S. design patent application Ser. No. 29/351,665 filed 9 Dec. 2009 entitled "Male dual lumen bayonet connector," which is hereby incorporated herein by reference in its entirety.

The present application is related to U.S. patent application Ser. No. 12/976 894 filed contemporaneously herewith entitled "Fluid connector latches profile lead-ins"; U.S. patent application Ser. No. 12/976 943 filed contemporaneously herewith entitled "Button latch with integrally molded cantilever springs"; and U.S. design patent application No. 29/352,637 filed 23 Dec. 2009 entitled "Female dual lumen connector," each of which is hereby incorporated herein by reference in its entirety.

BACKGROUND

1. Technical Field

The present disclosure relates generally to the field of medical devices used for the transport of both gaseous and liquid fluids and more specifically, to a male bayonet connector for creating a releasable air and fluid seal connection between one or more sections of tubing and a female latch connector.

2. Description of Related Art

Tubing sections, for example, medical tubing, must often be joined together to provide for gas and/or liquid fluid flow from one component to another. It is further often desirable to connect and disconnect tubing sections from one another. For example, when a patient's blood pressure is taken with an automatic blood pressure monitor, tubing from the blood pressure cuff (which is generally wrapped around the patient's arm) is connected to the tubing that is connected to the blood pressure monitor. To disconnect the cuff from the blood pressure monitor, it is desirable to merely detach the tubing section connected to the cuff from the tubing connected to the blood pressure monitor. Similarly, when providing intravenous fluids, it is often required to replace an empty fluid bag with a full fluid bag without removing the intravenous needle or stent from the patient. In order to switch between the first fluid bag and the second fluid bag, it is desirable to merely detach a tubing section connected with the fluid bag to the tubing section connected with the needle or stent placed intravenously in the patient, which can then be easily connected with a tubing section connected with the new fluid bag.

Existing tubing connectors are prone to leakage and unwanted disconnection when the patient is still receiving treatment via the connected tubes due to side-loads caused by the weight of the connected tubes and components, as well as accidental pulling of the tubes by the patient or medical personnel.

Furthermore, certain medical devices require the use of multiple tubes for supplying air or fluid between the patient and the device. For example, certain models of blood pressure monitors, such as the Dinamap Procare series, manufactured by General Electric, employ dual tubes for connecting the blood pressure cuff to the monitor. As such, a connector including multiple air passages for directing airflow between the tube segments is desirable, so as to avoid having to individually connect and disconnect multiple connectors when hooking or unhooking a patient to the monitor.

The information included in this Background section of the specification, including any references cited herein and any description or discussion thereof, is included for technical reference purposes only and is not to be regarded subject matter by which the scope of the invention is to be bound.

SUMMARY

A male bayonet connector may include a shaft defining a lumen therethrough and a grip that facilitates gripping of the shaft by the user. The outer surface of the shaft may define a tubing coupling for connecting with a section of tubing, an annular recess or channel that interfaces with a latch in a female connector for connecting the male bayonet connector with the female connector, and a sealing portion that engages a seal member or surface on an inner diameter of a receiving lumen within the female latch connector for creating a fluid seal between the male and female connectors.

In one implementation, a male bayonet connector includes a shaft defining a lumen and having a distal end portion and a proximal end portion. The proximal end portion of the shaft is configured to engage a section of tubing and the distal end portion of the shaft includes a sealing surface configured to engage a seal member on an inner diameter of a receiving lumen in the female latch connector to create a fluid-tight seal. The male bayonet connector further includes a grip that extends around at least a portion of the shaft. The shaft defines an annular recess proximal to and adjacent the distal end portion. The annular recess has a smaller diameter than the outer diameter of the sealing surface of the distal end portion. The annular recess has a proximal chamfered sidewall and a distal sidewall perpendicular to the axis of the lumen of the shaft. A ratio of a length of the sealing surface to a distance the grip and the distal sidewall is such that a side-load force of up to 10 lbs, as imparted on the male bayonet connector, will not break the fluid-tight seal between the sealing surface on the distal end of the shaft and the inner surface of the female receiving structure.

In another implementation, the perpendicular sidewall of the annular channel of the male bayonet connector defines a surface for interfacing with a latch structure within the female receiving structure that resists removal of the male bayonet connector from the female connector.

In another embodiment, the grip extends axially away from the shaft so as to define a flange around the shaft. The flange may define an outer edge and the grip may include a plurality of indentations along the outer edge of the flange for facilitating gripping of the grip.

In other embodiments, the beveled sidewall of the annular channel further defines an angle that is substantially 45 degrees with respect to an axis of the lumen of the shaft. In another embodiment, the ratio of the length of the sealing surface to the distance from the perpendicular sidewall to the grip may be between 0.889 and 1.105.

In another implementation, the male bayonet connector includes two parallel shafts each defining separate lumen and held together by the grip that extends around and between both shafts. The distance between the central axes of the lumen of the parallel shafts may be between 1.695 to 2.035 times the distance from the perpendicular sidewall to the grip.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. A more extensive presentation of features, details, utilities, and advantages of the present invention is provided in the following written description of various embodiments of the invention, illustrated in the accompanying drawings, and defined in the appended claims.

DETAILED DESCRIPTION

Male bayonet connectors, in conjunction with female latch connectors, may be used to releasably connect sections of tubing. In one embodiment, the male bayonet connector may have a single shaft portion defining a single lumen therethrough and an outer sealing surface that is configured to engage an inner surface of a female latch connector to form a gas and/or liquid fluid seal between the male and female components. The female latch connector may include a latching mechanism that engages a portion of the male bayonet connector so as to prevent removal of the male bayonet connector when connected with the female connector. In another embodiment, the male bayonet connector may have dual shafts, each defining a lumen therethrough. In alternative embodiments, the male bayonet connector may have three or more shafts defining three or more lumen. In embodiments of multiple lumen male bayonet connectors, a grip portion may be used to join the shaft portions, as well as tubing couplings that are configured to engage and retain multiple sections of tubing.

Figure 1:
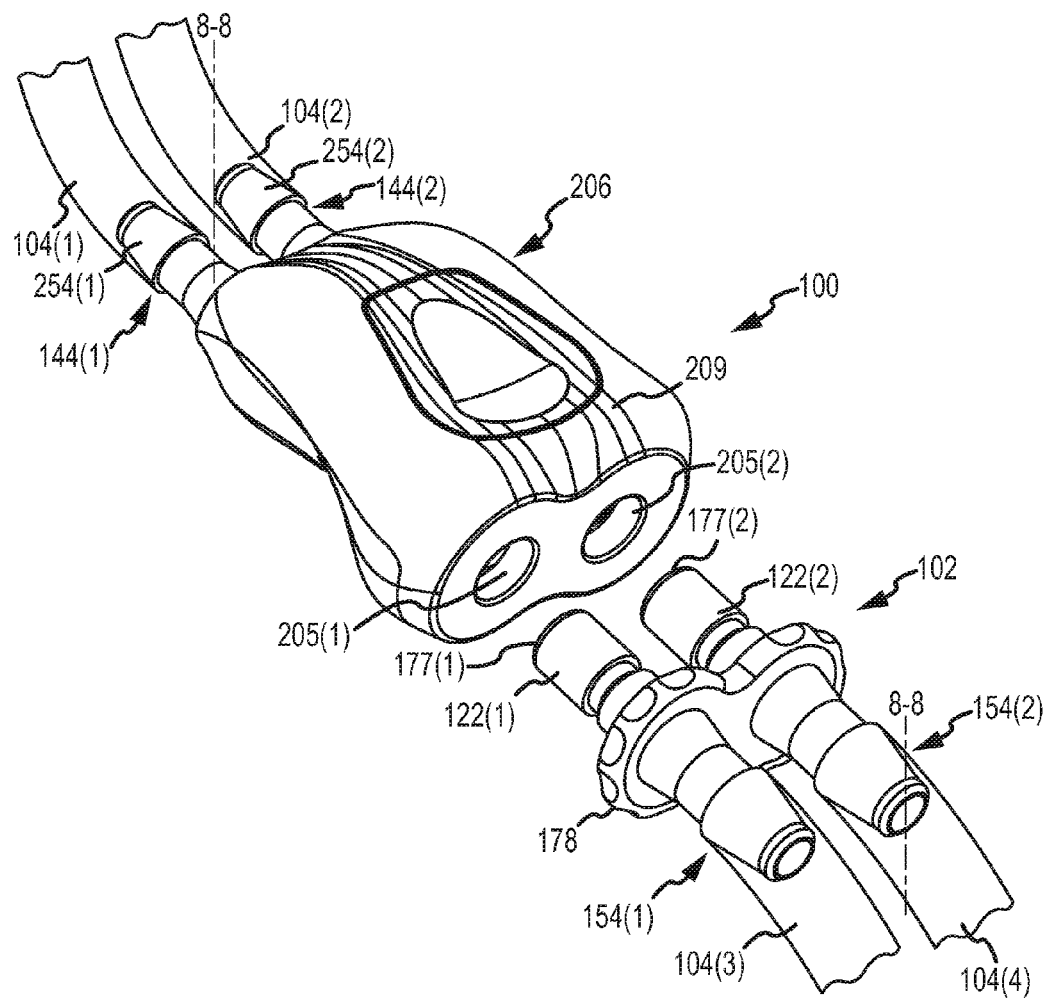
FIG. 1 is a front isometric view of a male dual bayonet connector, a female latch connector, and tube sections.

An examplary environment for a male dual bayonet connector 102 is illustrated in FIG. 1. The environment may include a releasable connection assembly 100 and tubing sections 104(1)-104(4). The releasable connection assembly 100 may include the male dual bayonet connector 102 and a female latch connector 206. The male dual bayonet connector 102 may be connected with the female latch connector 206 as will be described further with respect to FIGS. 11-13.

Referring to FIG. 1, first and second tubing sections 104 (1)-104(2) may connect with respective tubing couplings 144 (1)-144(2) on the distal end of the female latch connector 206. Third and fourth tubing sections 104(3)-104(3) may connect with respective tubing couplings 154(1)-154(2) on the proximal end of the male dual bayonet connector 102. As will be described further below, the male dual bayonet connector 102 may be connected with the female latch connector 206 by inserting the distal end of the male dual bayonet connector 102 into receiving openings 205(1)-205(2) defined in the proximal end of the female latch connector 206. The orientations "proximal" and "distal" as used herein have been arbitrarily chosen, and are not meant to limit the present disclosure, but will follow the convention just described with reference to the ends of the female latch connector 206 and male dual bayonet connector 102.

Figure 2:
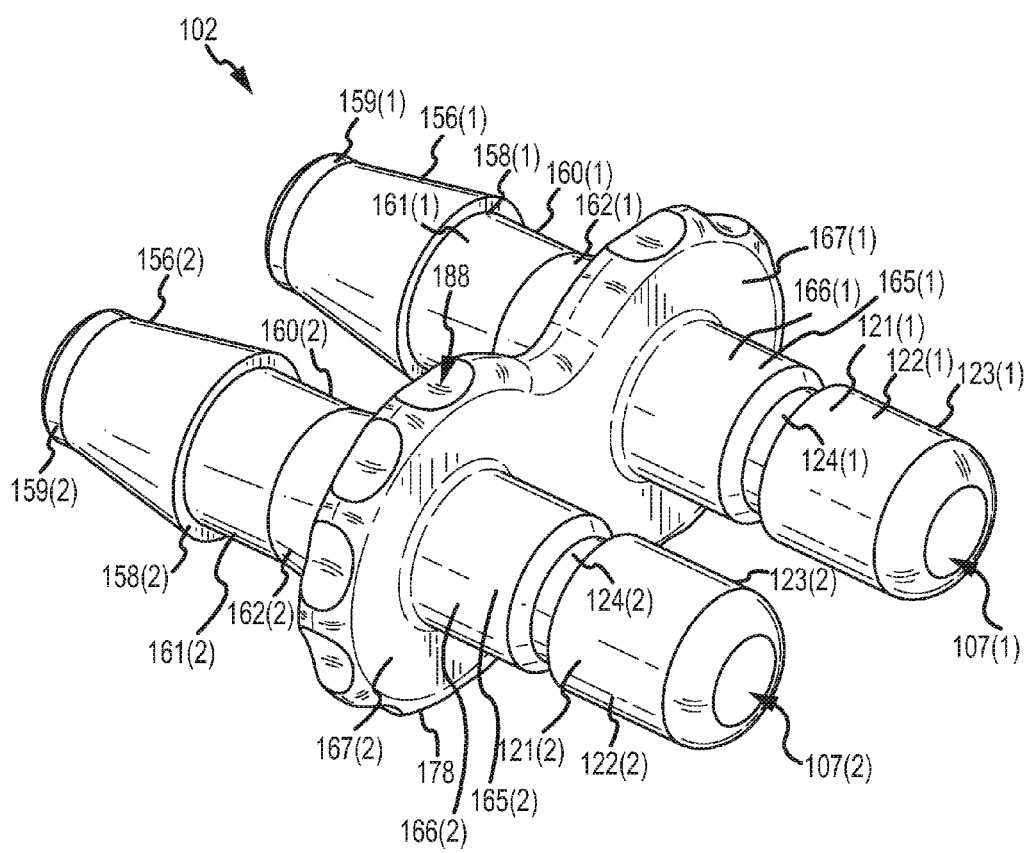
FIG. 2 is a rear isometric view of the male dual bayonet connector shown in FIG. 1.
Figure 3:
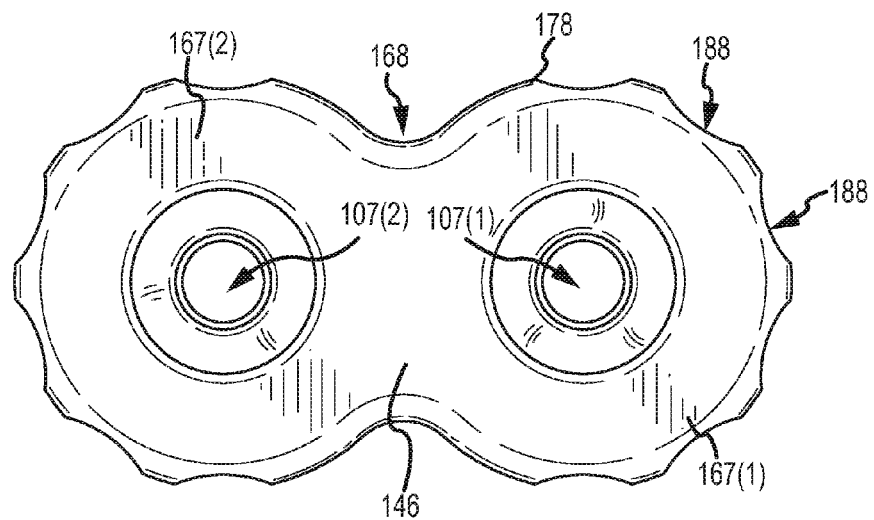
FIG. 3 is a front elevation view of the male dual bayonet connector shown in FIG. 1.
Figure 4:
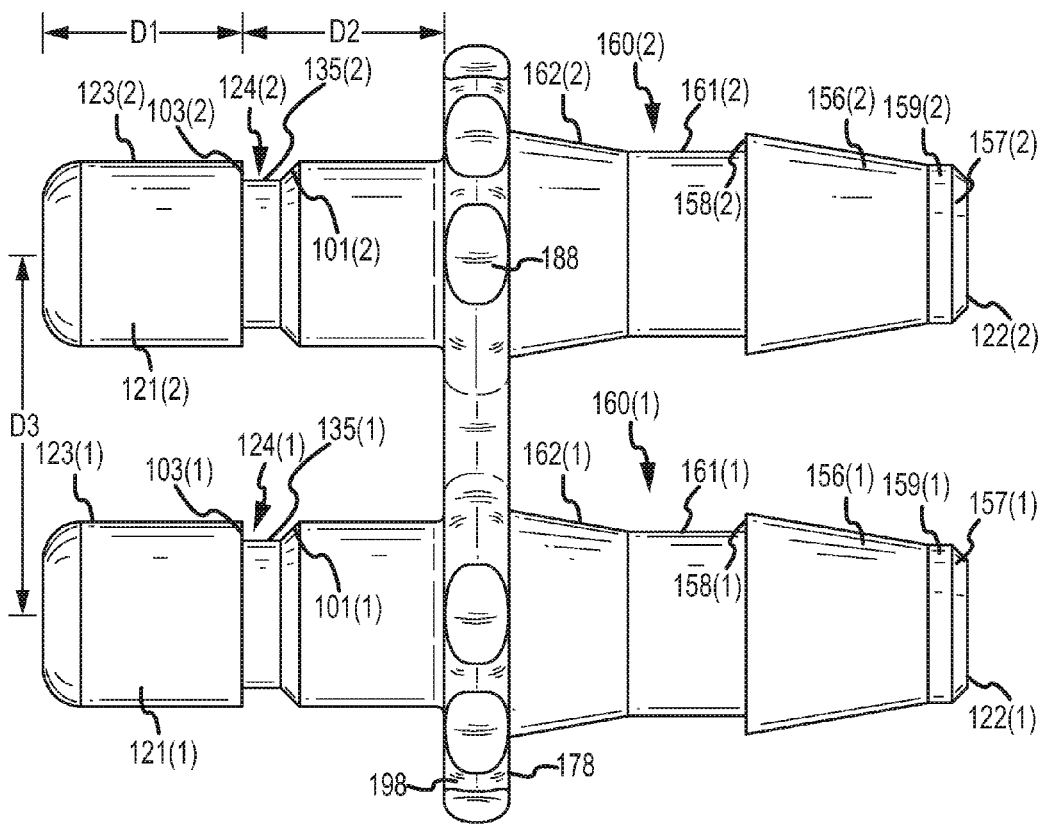
FIG. 4 is a top plan view of the male dual bayonet connector shown in FIG. 1.
Figure 5:
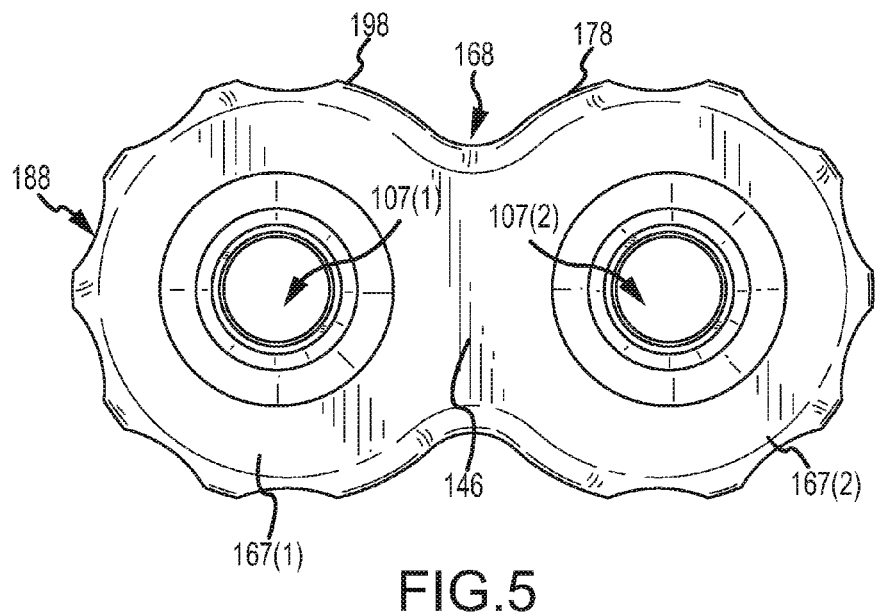
FIG. 5 is a rear elevation view of the male dual bayonet connector shown in FIG. 1.

The male dual bayonet connector 102 is illustrated in greater detail in FIGS. 2-6. The male dual bayonet connector 102 may include dual shafts 122(1)-122(2) connected by a grip 178. The dual shafts 122(1)-122(2) may extend from the proximal end of the male bayonet connector 102 to the distal end of the connector 102. As best seen in FIGS. 2, 3 and 5, each of the dual shafts 122(1)-122(2) may define a cylindrical lumen 107(1)-107(2) for transporting fluid from the third and fourth tubing sections 104(3)-104(4) coupled with the male dual bayonet connector 102 to the first and second tubing sections 104(1)-104(2) coupled with the female latch connector 206 via corresponding cylindrical lumens 227(1)-227(2) defined in the female latch connector 206. The dual cylindrical lumens 107(1)-107(2) of the shafts 122(1)-122(2) may be of substantially uniform diameter throughout the entire length of the dual shafts 122(1)-122(2) or, as best shown in cross-section in FIG. 3, may narrow or widen in diameter along the length of the shafts 122(1)-122(2) to include a smaller diameter section and a larger diameter section. In other embodiments, the diameter of the dual cylindrical lumens 107(1)-107(2) may be constant. In further embodiments, the portion of lumens 107(1)-107(2) in the tubing couplings 144(1)-144(2) may be radially offset with respect to the portion of the lumens 107(1)-107(2) along the length of the shafts 122(1)-122(2) to accommodate different tubing configurations. For example, the diameters of the dual cylindrical lumens 107(1)-107(2) may be larger and/or the tubing couplings 144(1)-144(2) may be spaced further or closer apart than the dual shafts 122(1)-122(2) to accommodate varying thicknesses of walls of tubing 104(1)-104(2).

The dual lumen configuration of the male dual bayonet connector 102 allows for simultaneously connecting and disconnecting two or more tubes using a single connection assembly, rather than requiring a separate connection assembly for each tube. As such, the male bayonet connector 102 may provide more efficient connecting and disconnecting of tubes by reducing the amount of time required for medical personnel to hook and unhook a patient from medical equipment.

Figure 6:
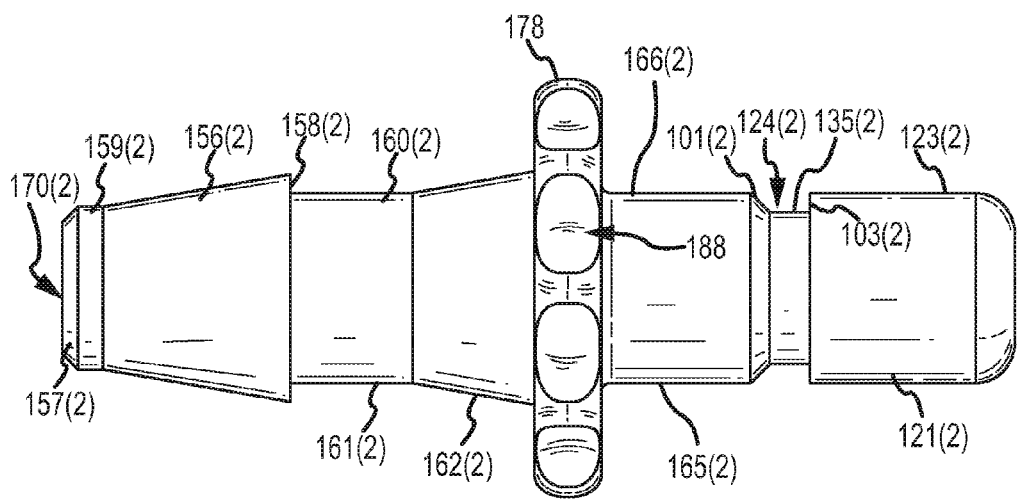
FIG. 6 is a side elevation view of the male dual bayonet connector shown in FIG. 1.

The proximal ends of the dual shafts 122(1)-122(2) may each include a coupling end 156(1)-156(2) shaped as a frustum tapering toward the proximal end for coupling with the third and fourth tube sections 104(3)-104(4) (as seen in FIG. 1). As best seen in FIGS. 4 and 6, the coupling ends 156(1)-156(2) may include a flattened region 159(1)-159(2) toward the proximal ends of the coupling ends 156(1)-156(2), i.e., at the smaller diameter of the frustum. The proximal ends of the coupling ends 156(1)-156(2) may further define a chamfered edge 157(1)-157(2). The exact angle of the chamfered edge 157(1)-157(2) may vary. For example, the chamfered edge 157(1)-157(2) may be between 30-55 degrees. In other embodiments, the proximal ends of the coupling ends 156(1)-156(2) may be rounded or perpendicular to the flattened region 159(1)-159(2). The overall tapered configuration of the coupling ends 156(1)-156(2), including the flattened regions 159(1)-159(2) and chamfered edges 157(1)-157(2) of the coupling ends 156(1)-156(2), may facilitate the insertion of the third and fourth tubing sections 104(3)-104(4) over the coupling ends 156(1)-156(2) of the dual shafts 122(1)-122(2).

The distal ends of the coupling ends 156(1)-156(2), i.e., at the larger diameter of the frustum, may be adjacent to a coupling shaft portion 160(1)-160(2) that may have a first portion 161(1)-161(2) having a narrower outer diameter than that of the distal end of the coupling end 156(1)-156(2), as well as a second portion 162(1)-162(2) that gradually widens in outer diameter toward the grip 178. As such, the coupling shaft portions 160(1)-160(2) may, in some embodiments, vary in outer diameter along the length of the shafts 122(1)-122(2), but in other embodiments, may have a substantially uniform outer diameter that may be narrower than the distal end of the coupling end 156(1)-156(2). The difference in outer diameters between the coupling ends 156(1)-156(2) and the first portions 161(1)-161(2) of the coupling shaft portions 160(1)-160(2) may result in an annular shelf that functions as a coupling barb 158(1)-158(2) for retaining the third and fourth tubing couplings 104(3)-104(4).

The distal ends of the shafts 122(1)-122(2) may define a sealing portion 121(1)-121(2) including a flattened sealing surface 123(1)-123(2). As will be described in further detail below, each sealing surface 123(1)-123(2) may engage a respective sealing member 270 (as shown in, e.g., FIGS. 11-13) in the female latch connector 206 to create a fluid-tight seal between the male dual bayonet connector 102 and the female latch connector 206. The distal end of the sealing portion 121(1)-121(2) may be rounded, as shown in FIGS. 4, 2 and 6, or, in other embodiments, may be chamfered or perpendicular to the sealing surface 123(1)-123(2).

The shafts 122(1)-122(2) may also include proximal portions 165(1)-165(2) defining a proximal shaft portion 166(1)-166(2) that extends toward a grip 178. The proximal shaft portions 166(1)-166(2) may have the same outer diameter as the sealing portion 121(1)-121(2). In one embodiment, the proximal shaft portions 166(1)-166(2) may have a uniform outer diameter. In other embodiments, the proximal shaft portions may have an outer diameter that is either larger or smaller than the outer diameter of the sealing portion 121(1)-121(2).

The shafts 122(1)-122(2) may also each include an annular channel 124(1)-124(2) between the proximal portions 165(1)-165(2) and the sealing portions 121(1)-121(2) that provides for locking of male dual bayonet connector 102 with the female latch connector 206. As shown in FIG. 3, the annular channels 124(1)-124(2) include a bottom region 135(1)-135(2) that has a smaller outer diameter than the outer diameter of the sealing portion 121(1)-121(2). The distal end of each annular channel 124(1)-124(2) is bounded by a distal sidewall 103(1)-103(2) perpendicular to the axes of the cylindrical lumens 107(1)-107(2). The depth of the annular channels 124(1)-124(2) is defined by the difference between the radius of the sealing portion 121(1)-121(2) and the radius of the bottom region 135(1)-135(2).

As best shown in the top and side views of the male dual bayonet connector 102 in FIGS. 4 and 6, the proximal end of each annular recess 124(1)-124(2) may be defined by a chamfered or beveled edge 101(1)-101(2). The beveled edge 101(1)-101(2) may define an angle with respect to the axes of the cylindrical lumens 107(1)-107(2). For example, the surface defined by each beveled edge 101(1)-101(2) may form a 45-degree angle with respect to the axes of the cylindrical lumens 107(1)-107(2). The beveled edge 101(1)-101(2) interfaces with the proximal side of the latch plate 200, which forces the male dual bayonet connector 102 proximally and holds the perpendicular sidewall against the latch plate 200 of the female latch connector 206 in the annular channels 124(1)-124(2). This interface reduces movement of the male dual bayonet connector 102 with respect to the female latch connector 206 and thereby reduces wear of the sealing member 207 in the female latch connector 206. In other embodiments, beveled edges 101(1)-101(2) may be perpendicular to the axes of the cylindrical lumens 107(1)-107(2), may be curved, or alternatively, may define any other angle between 0 and 90 degrees.

The length D1 of the sealing surfaces 123(1)-123(2) of the shafts 122(1)-122(2) as shown in FIG. 3 may bear a relationship to the distance D2 from the perpendicular sidewall 103(1)-103(2) of the annular channels 124(1)-124(2) to the grip 178. In one embodiment, the ratio of the length D1 of the sealing surfaces 123(1)-123(2) to the distance D2 from the perpendicular sidewall 103(1)-103(2) to the grip 178 may be such that a side-load force of up to 10 lbs, as imparted on the male bayonet connector 102, will not break the seal between the sealing surfaces 123(1)-123(2) and the sealing member 270 in the female connector 206. For example, in some implementations, the ratio of the length D1 to the distance D2 may be between 0.889 to 1.105.

A sealing surface 123(1)-123(2) that is proportionally substantially the same or longer with respect to the distance D2 from the annular shelf 103(1)-103(2) to the grip 178 may provide significant lateral support for the shafts 122(1)-122(2) when the male dual bayonet connector 102 is inserted into the female latch connector 206. This proportionality of the length of the shafts 122(1)-122(2) operates to increase resistance to side-load forces and prevent uneven force distribution along the sealing mechanism 270, such as when axial forces are applied to either the male dual bayonet connector 102 or the female latch connector 206. For example, the length of the sealing surface 123(1)-123(2) may allow for better lead-in alignment of the male dual bayonet connector 102 with the female latch connector 206. In addition, the length of the sealing surface 123(1)-123(2), when interfaced with a comparatively long supporting surface within the female latch connector 206, may further resist axial movement of the male dual bayonet connector 102 when connected to the female latch connector 206. The reduction of axial movement of the male dual bayonet connector 102 inside the female latch connector 206 may help resist the sealing member 270 from pinching or slipping off the distal end of the shaft 122(1)-122(2) and sustain contact between the interior surface of the sealing member 270 and the sealing surface 123(1)-123(2) to maintain a fluid-tight seal.

The length of the sealing surface 123(1)-123(2) further allows for positioning the sealing member 270 away from the distal end of the shaft 122(1)-122(2), so as to prevent the sealing member 270 from slipping off of the distal end of the shaft 122(1)-122(2) during engagement of the male dual lumen connector 102 with the female latch connector 206. For example, when interfacing with a supporting region in the female latch connector 206 that extends past the sealing member 270 toward the distal end of the shafts 122(1)-122(2), the engagement of the sealing surface 123(1)-123(2) and the female supporting region may resist axial misalignment of the shafts 122(1)-122(2) under side-loading, thus significantly reducing the possibility of generating a leak path. This serves as an improvement over bayonet designs where the majority of axial support for the shafts is provided at the distal end of the male connector, making these designs much more susceptible to axial and side-loading. Accordingly, the length D1 of the sealing portions 121(1)-121(2) of the shafts 122(1)-122(2) may be selected so as to optimize the stability of the male dual bayonet connector 102 when connected with the female latch connector206.

The male dual bayonet connector 102 may also include a grip 178, a portion of which may extend between the dual shafts 122(1)-122(2) to connect the shafts 122(1)-122(2) of the connector 102. In one embodiment, as best shown in FIGS. 7-11, the grip 178 includes two generally circular flanges 167(1)-167(2) that surround the shafts 122(1)-122(2) and that are concentric with the axes of the cylindrical lumens 107(1)-107(2). The flanges 167(1)-167(2) may be connected via a webbed portion 146 formed between the flanges 167(1)-167(2), and may have a larger outer diameter than the other portions of the shafts 122(1)-122(2) of the male dual bayonet connector 102. As such, the grip 178 may function as a stop for preventing over-insertion of the shafts 122(1)-122(2) into the female latch connector 206, and further as a guide for ensuring that the shafts 122(1)-122(2) are fully inserted into the female latch connector 206.

Figure 7:
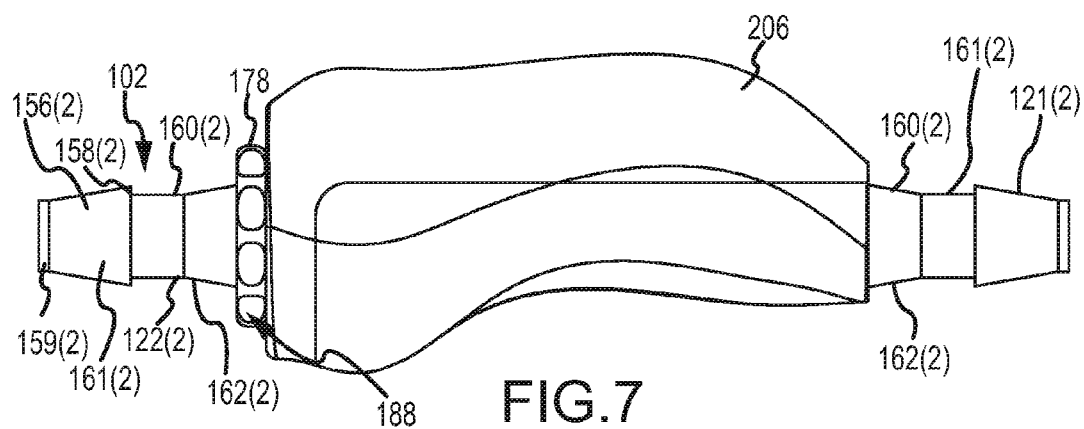
FIG. 7 is a side elevation view of the male dual bayonet connector, as connected to a female latch connector shown in FIG. 1.
Figure 8:
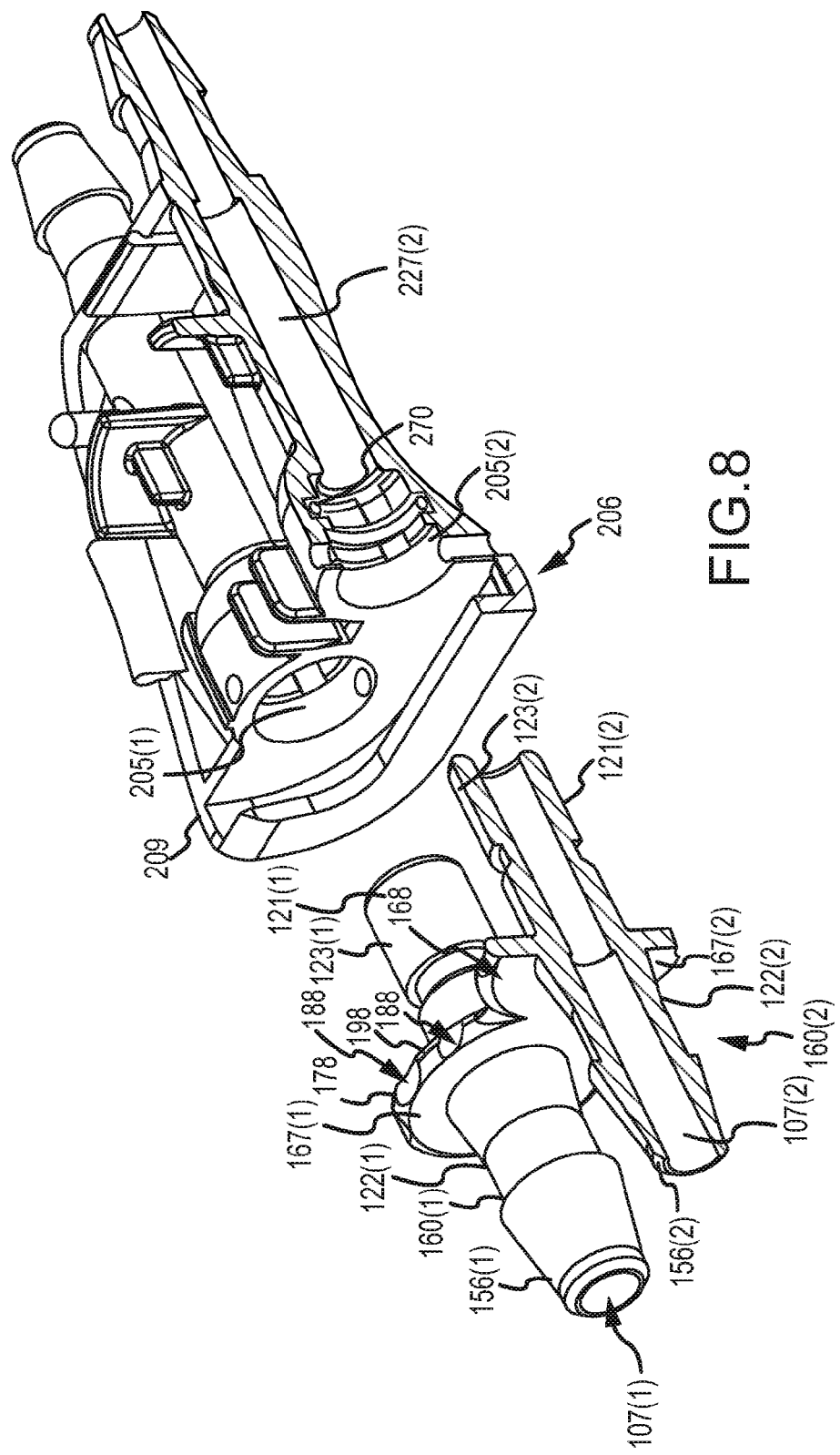
FIG. 8 is a rear isometric view of the male dual bayonet connector and female latch connector in cross section of the connecting member taken along line 8-8 of FIG. 1.
Figure 10:
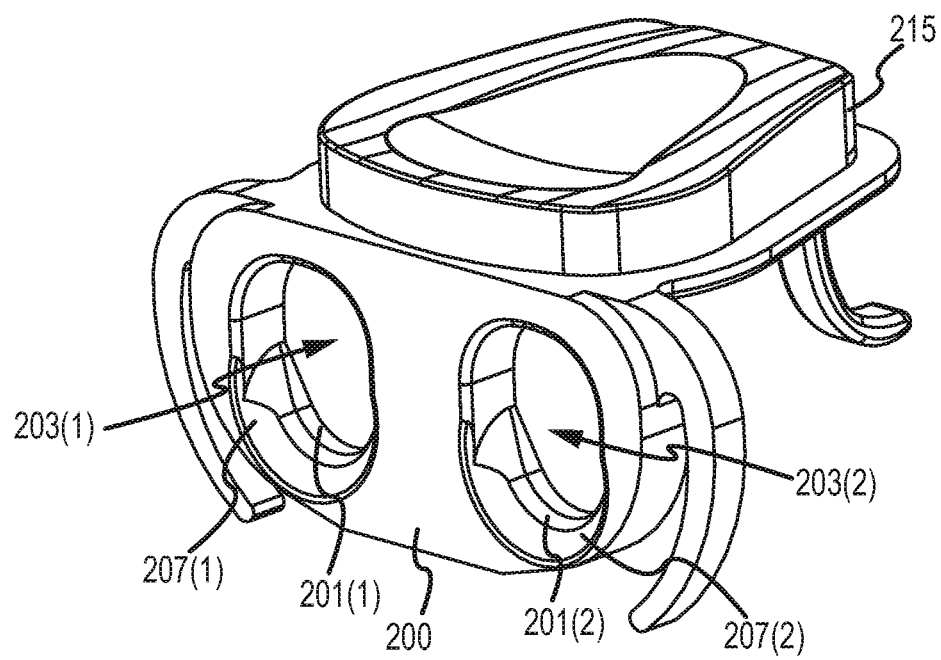
FIG. 10 is a front isometric view of a latch structure of the female latch connector.

As illustrated in FIGS. 7, 8 and 10, the webbed portion 146 may define a recessed area 168 between the flanges 167(1)-167(2) to allow for easy gripping of the male dual bayonet connector 102 when manipulated by a user. In addition to improving the grip of the male dual bayonet connector 102, providing a recessed area 168 in the webbed portion 146 between the flanges 167(1)-167(2) may further serve to reduce the amount of material required to manufacture the grip 178, thereby decreasing the overall cost associated with manufacturing the male dual bayonet connector 102. In alternate embodiments, there may not be a recessed area between the flanges 167(1)-167 (2) and the perimeter of the grip 178 may be in the form of an oval track with flat sidewalls.

The webbed portion 146 also provides a further benefit, in that it allows for optimal positioning of the lumens 107(1)-107(2) of the male dual bayonet connector 102 with respect to one another. In particular, the webbed portion 146 allows for positioning of the lumens 107(1)-107(2) so that the space between the central axes of the lumens 107(1)-107(2) can be maximized to allow for convenient connection and removal of both individual and webbed tubes, i.e., tubes connected with an intermediate web along their length, without modifying the tubing. In one embodiment, a distance D3 between the axes of the lumens 107(1)-107(2) may be between approximately 1.695 to 2.035 times the length D2 between the perpendicular sidewall 103(1)-103(2) and the grip 178. Additionally, a wider webbed portion 146 may position the lumens 107(1)-107(2) further apart and may help prevent tangling of the attached tubing, while a narrower webbed portion 146 would position the lumens 107(1)-107(2) closer together. A wider webbed portion 146 may alternatively allow for thicker-walled tubing to be attached to the male dual bayonet connector 102 by providing sufficient clearance for thicker tube walls. Accordingly, the width of the webbed portion 146 may be varied according to the specifications of the tubing being attached to the male dual bayonet connector 102.

Additionally, the outer edge 198 of the grip 178 may include one or more evenly-spaced indentations 188 to further facilitate gripping of the male dual bayonet connector 102 by a user. In the embodiment illustrated in FIGS. 2-6, the outer edge 198 of the grip 178 includes twelve (12) evenly-spaced indentations 188, with each ring 167(1)-167(2) including six (6) indentations 188, and a recessed webbed portion 146 extending between the rings 167(1)-167(2). However, the exact number, shape, and size of the indentations 188 is not critical so long as the grip 178 provides an enhanced gripping surface for the user. As such, in other embodiments, the number, shape, and size of the indentations 188 along the grip 178 may vary.

Another function of the grip 178 is to provide proper lead-in alignment of the male dual bayonet connector 102 with the female latch connector 206, thereby allowing for proper insertion of the male dual bayonet connector 102 into the female latch connector 206. Furthermore, the grip 178 ensures axial alignment of the shafts 122(1)-122(2) with the receiving openings 205(1)-205(2) of the female latch connector 206 during engagement, so as to allow for even distribution of the pressure applied by the sealing surface 123(1)-123 (2) against the sealing member 270 to prevent leakage around the sealing surface 123(1)-123(2), as well as deformation and/or uneven wearing of the sealing member 270 over time.

In a further embodiment, a flat rib (not shown) may extend between the proximal portions 165(1)-165(2) of the shafts 122(1)-122(2) to provide greater structural rigidity to the male dual lumen connector 102. The length and thickness of the rib may vary depending upon design requirements or constraints or with the relative durometer of the material used to form the connector 102. The rib may or may not be connected to the webbed portion 146 of the grip 178.

Figure 9:
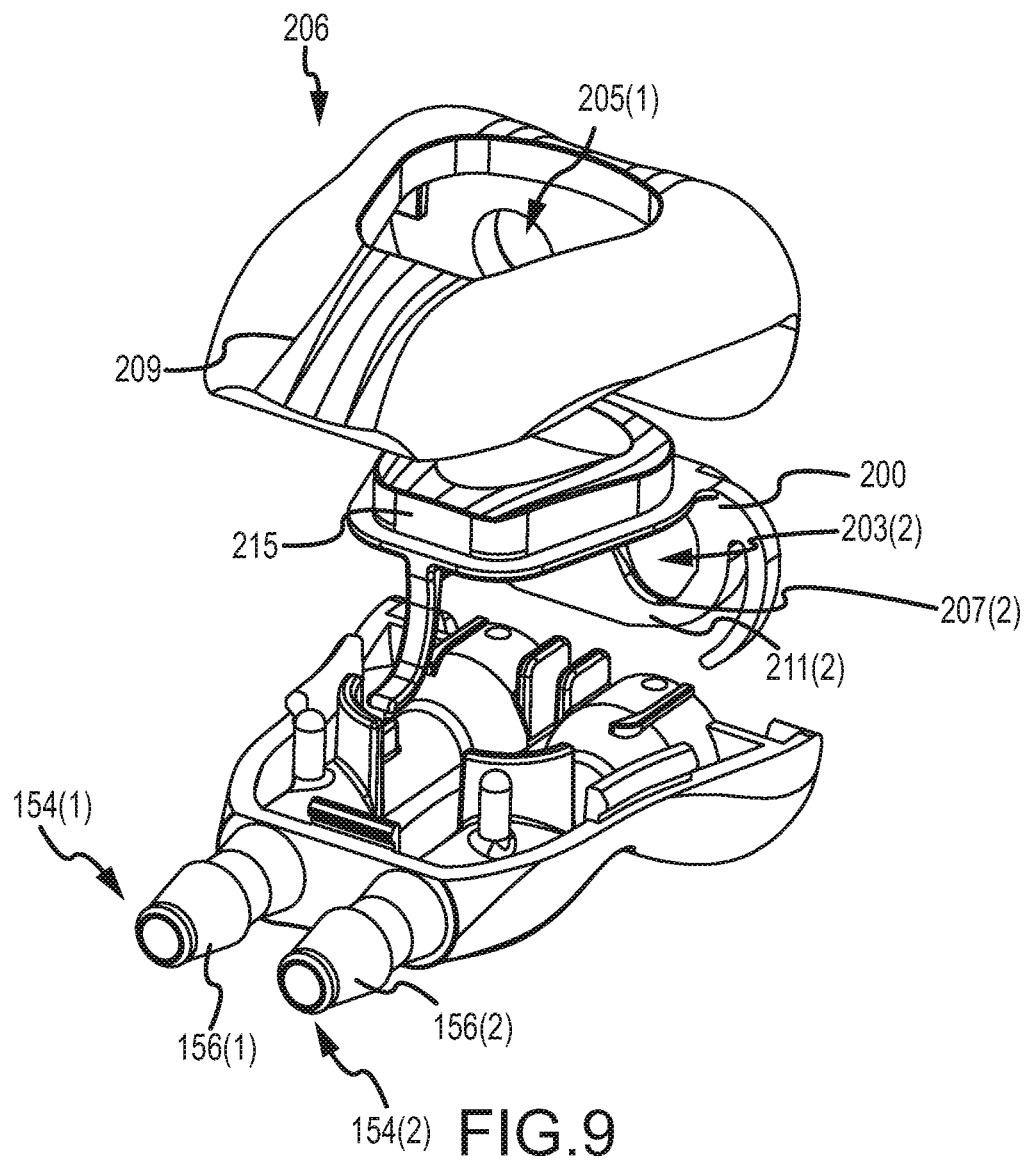
FIG. 9 is an exploded rear isometric view of the female latch connector shown in FIG. 1.

One embodiment of a female latch connector 206 that may be connected to the male dual bayonet connector 102 is illustrated in FIGS. 8-10. The female latch connector 206 may include an exterior enclosure 209 defining two openings 205 (1)-205(2) for receiving the dual shafts 122(1)-122(2) of the male dual bayonet connector 102. As shown in FIG. 7, the female latch connector 206 may further include a latch plate structure 200 defining two receiving apertures 203(1)-203(2) that are axially aligned with the exterior openings 205(1)-205 (1) of the assembled female latch connector 206, so as to receive the shafts 122(1)-122(2).

The female latch connector 206 may further define two cylindrical lumens 227(1)-227(2) that extend through the female latch connector 206. In one embodiment, the cylindrical lumens 227(1)-227(2) of the female latch connector 206 are positioned so that when the female latch connector 206 and the male dual lumen connector 102 are connected, the female lumens 227(1)-227(1) are axially aligned with at least a portion of the male cylindrical lumens 107(1)-107(2) to facilitate fluid flow between the connected male and female connectors 102 and 206. In other embodiments, sections of the lumens 107(1)-107(2) and 227(1)-227(2) of the male 102 or female 206 connectors may be offset with respect to one another. Additionally, the female latch connector 206 may include two tubing couplings 254(1)-254(2) that are each configured to engage a section of tubing 104(1)-104(2), as shown in FIG. 1. The tubing couplings 254(1)-254(2) of the female latch connector 206 may be similar in configuration to the male tubing couplings 156(1)-156(2)

The latch plate structure 200 of the female latch connector 206 is shown in FIGS. 9 and 10. As best seen in FIG. 10, latching surfaces 201(1)-201(2) may be formed along the bottom walls of the receiving apertures 203(1)-203(2) of the latch plate structure 200. In one embodiment, the latch plate 200 may be resiliently biased upward to lift the latching surfaces 201(1)-201(2) so as to interface with the annular channels 124(1)-124(2) in the male dual bayonet connector 102. For example, as the shafts 122(1)-122(2) are inserted through the apertures 203(1)-203(2), the latch plate 200 may be biased downward to lower the receiving apertures 203(1)-203(2) to accommodate the outer diameter of the shafts 122(1)-122(2). In one embodiment, the receiving apertures 203(1)-203(2) may each be defined by a chamfered edge 207(1)-207(2) that is angled to facilitate the insertion of the shafts 122(1)-122(2) through the receiving apertures 203(1)-203(2) of the latch structure 200. The distal face of the latch plate 200 may define distal latching edges 211(1)-211(2) that may interface with the annular shelves 103(1)-103(2) of the shafts 122(1)-122(2) to prevent the shafts 122(1)-122(2) from being removed from the female latch connector 206.

The latch surfaces 201(1)-201(2) may be operably coupled to a release mechanism 215 for disengaging the latch surfaces 201(1)-201(2) from the male dual bayonet connector 102. For example, as shown in FIGS. 1, 9 and 10, the release mechanism 215 may be a button that, when depressed, may lower the latch plate 200 so that the latch surfaces 201(1)-201(2) may clear the annular channels 124(1)-124(2), allowing for removal of the shafts 122(1)-122(2) from the receiving apertures 205(1)-205(2) of the female latch connector 206.

The female latch connector 206 may further include a sealing member 270 that engages the sealing surface 123(1)-123(2) of the dual shafts 122(1)-122(2) to form a fluid-tight seal between the female receiving portion 206 and the male dual bayonet connector 102. The sealing member 270 may be made from an elastomeric material that may enhance the sealing interface between the female sealing member 270 and the sealing surface 123(1)-123(2) of the male dual bayonet connector 102.

Figure 11:
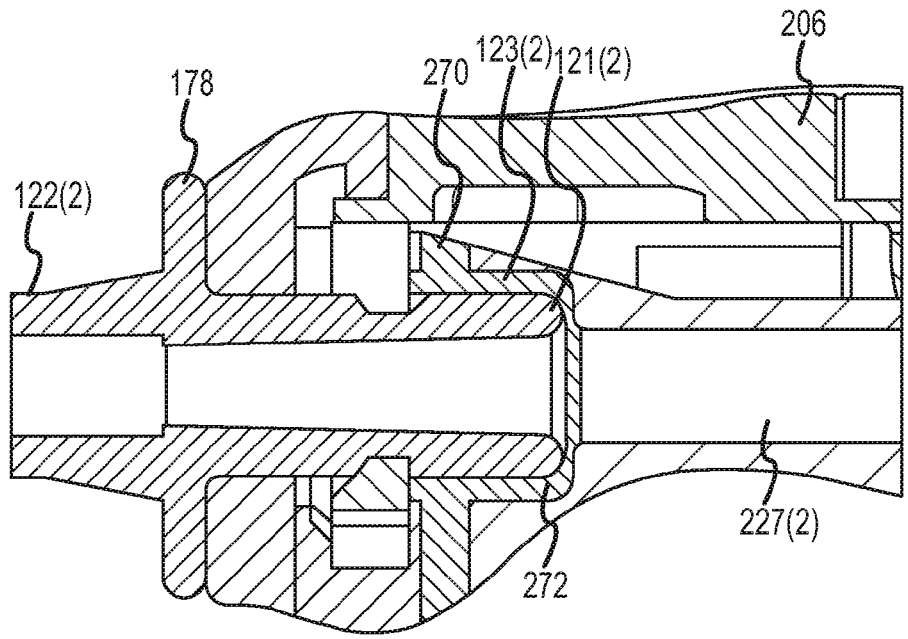
FIG. 11 is a side elevation view in cross-section of another embodiment of the male dual bayonet connector.
Figure 12:
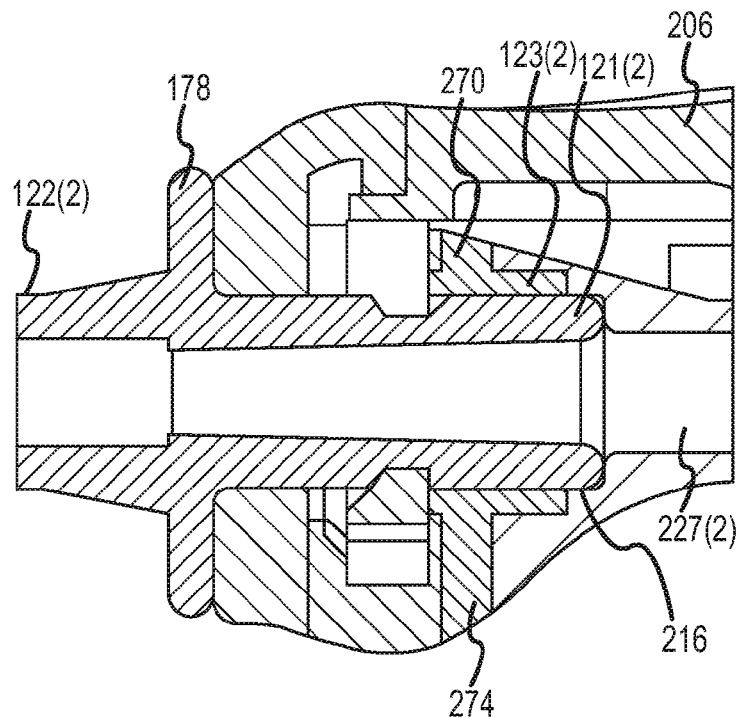
FIG. 12 is a side elevation view in cross-section of another embodiment of the male dual bayonet connector.
Figure 13:
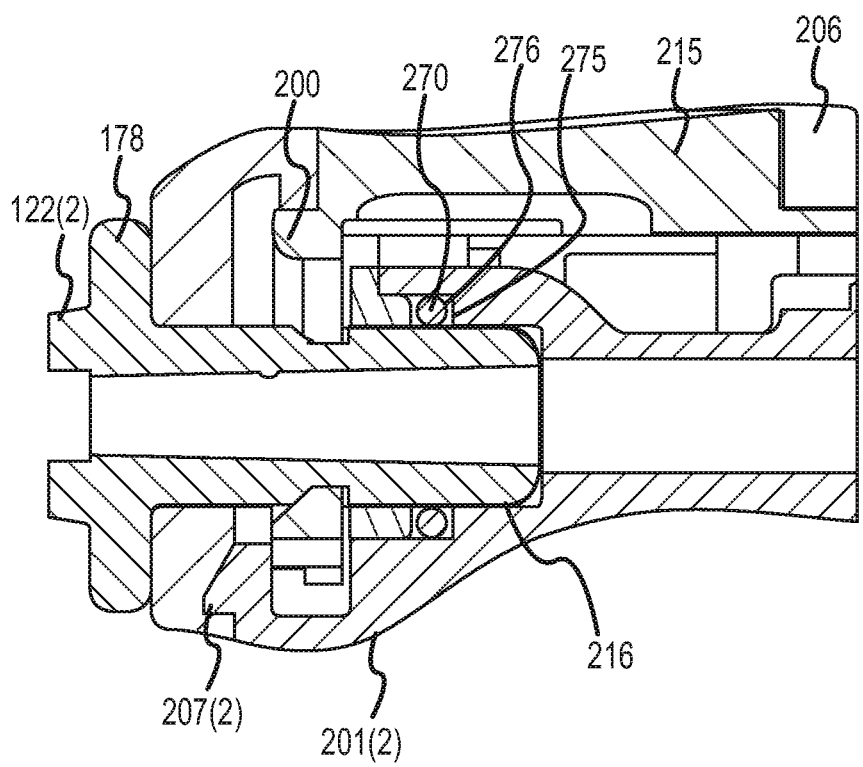
FIG. 13 is a side elevation view in cross-section of another embodiment of the male dual bayonet connector.

As best shown in FIGS. 11-13, illustrating the female latch connector 206 connected to the male dual bayonet connector 102, the configuration of the sealing member 270 within the female receiving portion 206 may vary according to different embodiments of the female receiving portion 206. As shown in FIG. 9, in one embodiment, the sealing member 270 may be an over-molded seal 272 that extends along the entire length D1 of the sealing portion 121(1)-121(2) so as to cover the entire sealing surface 123(1)-123(2), as well as forming and end seal with the distal end of the male dual bayonet connector 102. In another embodiment, illustrated in FIG. 10, the sealing member 270 may be an over-molded seal 274 that may cover only a portion of the length D1 of the sealing surface 123(1)-123(2). In yet another embodiment, illustrated in FIG. 11, the sealing member 270 may include an O-ring 276 that has a point contact with the sealing surface 123(1)-123(2). The O-ring 276 may be seated within a recessed area 275 defined by the female latch connector 206.

To connect the male dual bayonet connector 102 with the female latch connector 206, the dual shafts 122(1)-122(2) may be inserted through the openings 205(1)-205(2) (shown in FIG. 1) defined in the exterior enclosure 209 of the female latch connector 206 and the apertures 203(1)-203(2) defined by the latch plate structure 200. Insertion of the shafts 122(1)-122(2) through the apertures 203(1)-203(2) of the latch plate structure 200 causes the latch plate 200 to lower due to the interaction between the rounded distal ends 177(1)-177(2) of the shafts 122(1)-122(2) and the chamfered edges 207(1)-207(2) of the latch surfaces 201(1)-201(2).

Once the shafts 122(1)-122(2) are inserted far enough so that the latch surfaces 201(1)-201(2) are positioned below the annular channels 124(1)-124(2), the latch plate structure 200 may lift so that at least a portion of the latch surfaces 201(1)-201(2) is at least partially seated within the annular channels 124(1)-124(2). As best shown in cross section in FIGS. 9-11, the beveled edges 101(1)-101(2) defined by the annular channels 124(1)-124(2) may be angled to oppose the angle defined by the chamfered edges 207(1)-207(2) of the latch surfaces 201(1)-201(2), thereby preventing lateral movement of the male dual bayonet connector 102 with respect to the connected female latch connector 206.

The distal latching edges 211(1)-211(2) of the latch plate 200 may interface with the perpendicular distal sidewall 103(1)-103(2) of the annular channels 124(1)-124(2) so as to prevent removal of the shafts 122(1)-122(2) from the female receiving portion 206. The perpendicular distal sidewalls 103(1)-103(2) resist disengagement from the latch plate 200 under longitudinal and axial loads. In one embodiment, the distal latching edges 211(1)-211(2) of the latch face 200 may oppose the perpendicular distal sidewalls 103(1)-103(2) defined in the shafts 122(1)-122(2) to provide a greater axial retention force, as well as the ability to lock the male dual bayonet connector 102 with the female receiving portion 206 from the bottom of the shafts 122(1)-122(2), as opposed to the sides of the shafts 122(1)-122(2). This bottom locking feature further lessens the distance required for lowering the latch plate 200 to release the male dual bayonet connector 102, thereby improving the overall ergonomic design of the female latch connector 206 and minimizing the insertion force required for inserting the male dual bayonet connector 102 into the female latch connector 206.

The elongated sealing surface 123(1)-123(2) of the shafts 122(1)-122(2) may allow for positioning of the sealing mechanism 270 away from the distal end of the sealing surface 123(1)-123(2). As discussed above, this may help prevent the sealing mechanism 270 from pinching or slipping off from the distal end of the shaft 122(1)-122(2), and to sustain contact between the interior surface of the sealing mechanism 270 and the sealing surface 123(1)-123(2) to maintain a fluid-tight seal when axial forces are applied to either of the connected the male dual bayonet connector 102 or the female latch connector 206. In some embodiments, such as when the female latch connector 206 includes an O-ring 276 or partial molded seal 274, the female latch connector 206 may include an additional supporting surface 216 that is positioned around the distal end of the shafts 122(1)-122(2) for providing additional axial support for the shafts 122(1)-122(2), and further preventing deformation of the sealing mechanism 270.

To remove the male dual bayonet connector 102 from the female receiving portion 206, a user may depress the release mechanism 215 to lower the latch plate 200 until the latch surfaces 201(1)-201(2) clear the annular channels 124(1)-124(2). Once the annular channels 124(1)-124(2) are cleared, the male dual bayonet connector 102 may be easily disengaged from the female latch connector 206.

Figure 14:
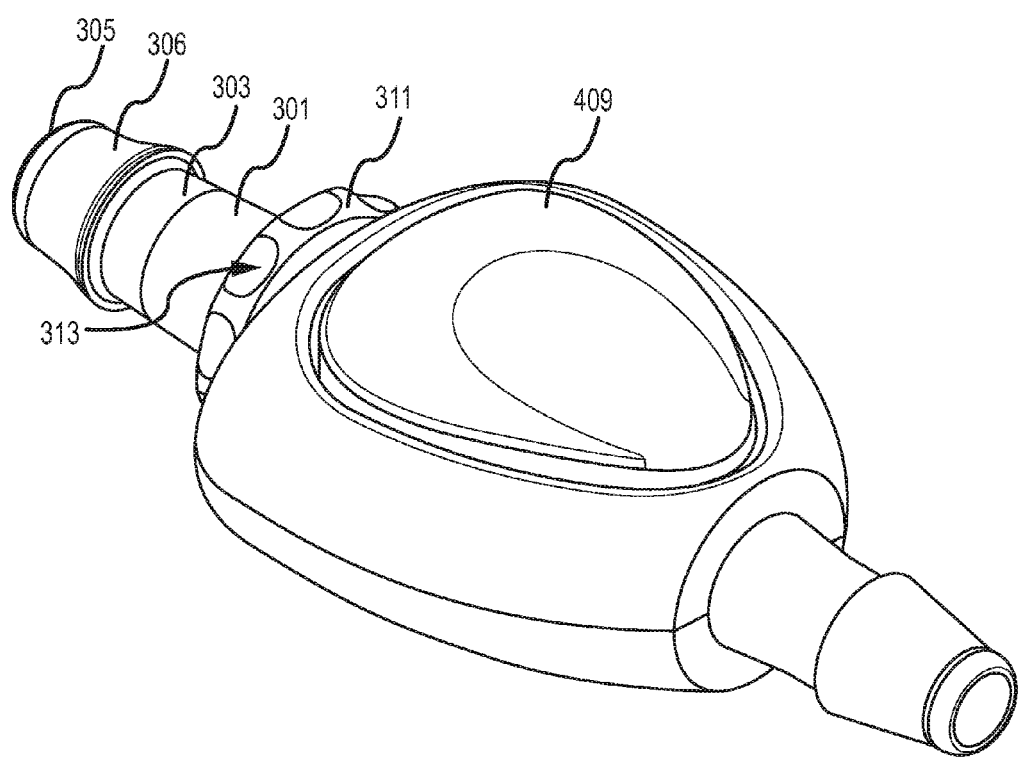
FIG. 14 is a rear isometric view of a male bayonet connector and female latch connector.
Figure 15:
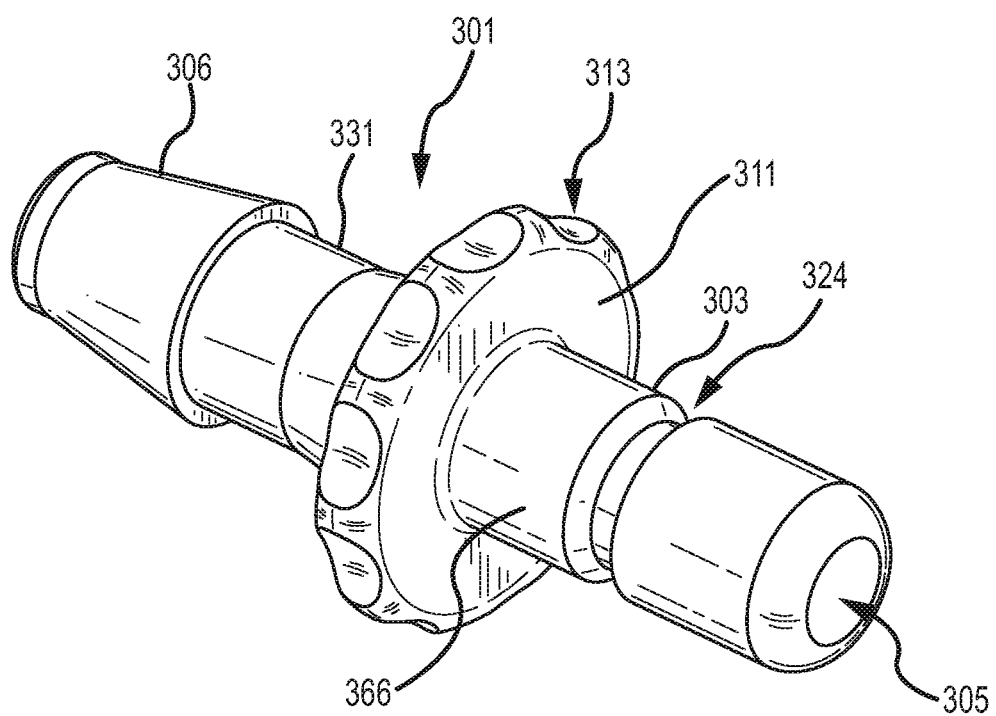
FIG. 15 is a rear isometric view of a male bayonet connector.

FIGS. 14 and 15 illustrate a single-lumen embodiment of the male bayonet connector 301. In this embodiment, the male bayonet connector 301 may include a single shaft 303, and a single lumen 305 extending through the length of the shaft 303. Similar to the male dual bayonet connector 102, the proximal end of the male bayonet connector 301 may include a coupling end 306 for connecting with a tubing section. The tubing coupling 306 may have a configuration similar to the coupling ends 156(1)-156(2) of the male dual bayonet connector 102 illustrated in FIGS. 2-6. The shaft 303 may further include a coupling shaft portion 331 similar to the coupling shaft portions 160(1)-160(2) of the male bayonet connector 102, and a proximal shaft portion 366 similar in configuration to the proximal shaft portions 166(1)-166(2) of the connector 102. The distal end of the male bayonet connector 301 may include a sealing surface similar to the flattened sealing surface 123(1)-123(2) of the male dual bayonet connector 102 illustrated in FIGS. 2-6, as well as an annular channel 324 that is configured similar to the annular channels 124(1)-124(2) of the male dual bayonet connector 102. In addition, the male bayonet connector 301 may include a ring-shaped grip 311 including a plurality of indentations 313 along the outer edge thereof. In one embodiment, the grip 311 of the male bayonet connector 301 may include ten (10) indentations.

As shown in FIG. 14, the female connector 409 may include a latch plate structure that is similar to the latch plate structure 200 of the female latch connector 206. The latch plate of the female connector 209 may include a single aperture for receiving the shaft 303 of the male bayonet connector 301. Additionally, the female connector 209 may include a sealing mechanism similar to the sealing mechanisms 270 shown in FIGS. 9-11. When connected, the latch plate may interface with the annular channel of the shaft 303, and the sealing mechanism may interface with the male sealing surface in a manner similar to that previously described with respect to FIGS. 11-13. Other embodiments of male bayonet connectors and female latch connectors may include any number of lumens, barbs, and associated shaft portions, as appropriate for the medical procedure being performed.

It will be apparent to those of ordinary skill in the art that variations and alternative embodiments may be made given the foregoing description. Such variations and alternative embodiments are accordingly considered within the scope of the present invention.

As used herein, lumen refers not only to its definition, but also refers to an opening, aperture, or other passageway. The fluid referred to herein can be gaseous, liquid, or other state of material that is flowable through a tube (i.e., granular). In addition, while generally described above as sealed when connected together, the connector structures may be sealed or unsealed. The connection between the male dual bayonet connector and female latch connectors and their respective tube sections can be by means other than a barbed fitting, for example, but not limited to, threaded, press-fit without a barb, John Guest fitting, ferrule, and panel mount.

All directional references (e.g., upper, lower, upward, downward, left, right, leftward, rightward, top, bottom, above, below, inner, outer, vertical, horizontal, clockwise, and counterclockwise) are only used for identification purposes to aid the reader's understanding of the example of the invention, and do not create limitations, particularly as to the position, orientation, or use of the invention unless specifically set forth in the claims. Joinder references (e.g., attached, coupled, connected, joined, and the like) are to be construed broadly and may include intermediate members between a connection of elements and relative movement between elements. As such, joinder references do not necessarily infer that two elements are directly connected and in fixed relation to each other.

In some instances, components are described with reference to "ends" having a particular characteristic and/or being connected with another part. However, those skilled in the art will recognize that the present invention is not limited to components which terminate immediately beyond their points of connection with other parts. Thus, the term "end" should be interpreted broadly, in a manner that includes areas adjacent, rearward, forward of, or otherwise near the terminus of a particular element, link, component, part, member or the like. In methodologies directly or indirectly set forth herein, various steps and operations are described in one possible order of operation, but those skilled in the art will recognize that steps and operations may be rearranged, replaced, or eliminated without necessarily departing from the spirit and scope of the present invention.

The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the spirit or scope of this invention. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

What is claimed is:

1. A male bayonet connector for connecting sections of tubing, the male bayonet connector comprising:
a first shaft including a first distal end portion, a first proximal end portion, and a first annular channel proximal to and adjacent the first distal end portion, a first lumen being defined between the first distal end portion and the first proximal end portion; and
a grip attached to at least a portion of the first shaft, wherein:
the first proximal end portion of the first shaft is configured to engage a first section of tubing;
the first distal end portion of the first shaft has a first sealing surface configured to engage a first inner surface of a female receiving structure to create a fluid-tight seal;
the first sealing surface has a constant diameter along a portion of its axial length and extends distally from the first annular channel; and
the first annular channel is defined by a first distal sidewall that is perpendicular with respect to an axis of the first lumen, a first proximal sidewall having a first beveled edge, and a first bottom region connecting the first distal sidewall and the first beveled edge, with the first bottom region being concentric and recessed radially inward with respect to the first sealing surface.

2. The male bayonet connector of claim 1, wherein the first distal sidewall defines a surface for interfacing with a first latch structure within the female receiving structure so as to prevent removal of the male bayonet connector from the female receiving structure when the first latch structure engages the first annular channel.

3. The male bayonet connector of claim 1, wherein the grip extends radially away from the first shaft so as to define a flange around the first shaft.

4. The male bayonet connector of claim 3, wherein the flange defines an outer edge and the grip includes a plurality of indentations along the outer edge of the flange for facilitating gripping of the grip.

5. The male bayonet connector of claim 1, wherein a ratio of an axial length of the first sealing surface to an axial distance between the first distal sidewall and the grip is between 0.889 and 1.105.

6. The male bayonet connector of claim 1, wherein a surface of the first beveled edge defines an angle that is substantially 45 degrees with respect to an axis of the first lumen.

7. The male bayonet connector of claim 1, wherein the grip is positioned to prevent further insertion of the first shaft into the female receiving structure.

8. The male bayonet connector of claim 1, further comprising:
a second shaft including a second distal end portion, a second proximal end portion, and a second annular channel proximal to and adjacent the second distal end portion, a second lumen being defined between the second distal end portion and the second proximal end portion, wherein:

the second proximal end portion of the second shaft is configured to engage a second section of tubing;

the second distal end portion of the second shaft has a second sealing surface configured to engage a second inner surface of the female receiving structure to create a fluid-tight seal; and the second sealing surface has a constant diameter along a portion of its axial length and extends distally from the second annular channel.

9. The male bayonet connector of claim 8, wherein the grip connects the first and second shafts.

10. The male bayonet connector of claim 9, wherein the grip extends away from the first shaft so as to define a first flange around the first shaft and extends away from the second shaft so as to define a second flange around the second shaft, and the first and second flanges are connected by a webbed portion therebetween.

11. The male bayonet connector of claim 10, wherein the webbed portion defines a recessed area between the first and second flanges.

12. The male bayonet connector of claim 10, wherein the grip defines a larger outer diameter than any other portion of the first or second shafts.

13. The male bayonet connector of claim 8, wherein a distance between a first central axis of the first lumen and a second central axis of the second lumen is between 1.695 to 2.035 times the distance between the first distal sidewall and the grip.

14. The male bayonet connector of claim 8, wherein the second annular channel is defined by a second distal sidewall that is perpendicular with respect to an axis of the second lumen, a second proximal sidewall having a second beveled edge, and a second bottom region connecting the second distal sidewall and the second beveled edge, with the second bottom region being concentric and recessed radially inward with respect to the second sealing surface.

15. The male bayonet connector of claim 14, wherein:

a ratio of a first axial length of the first sealing surface to a first axial distance between the first distal sidewall and the grip is between 0.889 and 1.105; and a ratio of a second axial length of the second sealing surface to a second axial distance between the second distal sidewall and the grip is between 0.889 and 1.105.

16. The male bayonet connector of claim 15, wherein:

the first axial length and the second axial length are equivalent; and the first axial distance and the second axial distance are equivalent.

17. The male bayonet connector of claim 14, wherein:

a ratio of the axial length of the first sealing surface to a distance between the first distal sidewall and the grip is such that a side-load force of up to 10 lbs, as imparted on the male bayonet connector, will not break the fluid-tight seal between the first sealing surface and the first inner surface of the female receiving structure; and a ratio of the axial length of the second sealing surface to a distance between the second distal sidewall and the grip is such that a side-load force of up to 10 lbs, as imparted on the male bayonet connector, will not break the fluid-tight seal between the second sealing surface and the second inner surface of the female receiving structure.

18. The male bayonet connector of claim 1, wherein the grip extends at least a portion of the first shaft.

19. The male bayonet connector of claim 1, wherein a ratio of the axial length of the first sealing surface to a distance between the first distal sidewall and the grip is such that a side-load force of up to 10 lbs, as imparted on the male bayonet connector, will not break the fluid-tight seal between the first sealing surface and the first inner surface of the female receiving structure.

20. A male bayonet connector for connecting sections of tubing, the male bayonet connector comprising:

a shaft comprising:

a distal end portion defining a sealing surface of constant diameter configured to engage a receiving portion of a female receiving structure;

a proximal end portion configured to engage a section of tubing; and an annular channel proximal to and adjacent the distal end portion and recessed with respect to the diameter of the sealing surface, the shaft further defining an axial lumen;

the annular channel further comprising:

a distal sidewall that is perpendicular with respect to an axis of the axial lumen;

a proximal sidewall having a beveled edge; and a grip extending around at least a portion of the shaft wherein:

the sealing surface has a constant diameter along a portion of its axial length and extends distally from the distal sidewall of the annular channel; and a ratio of an axial distance between the distal end portion to the distal sidewall and an axial distance between the distal sidewall and the grip is between 0.889 and 1.105.

21. A dual lumen male bayonet connector for connecting sections of tubing to a quick release coupler, the dual lumen male bayonet connector comprising:

a first shaft; and a second shaft spaced apart from and connected to the first shaft, each of the first shaft and the second shaft comprising:

a distal sealing portion defining a sealing surface configured to engage a receiving portion of a female receiving structure of the quick release coupler;

a proximal coupling portion configured to engage a section of tubing; and an annular channel proximal to and adjacent the distal sealing portion, each of the first shaft and the second shaft further defining an axial lumen;

the annular channel of each of the first shaft and the second shaft comprising:

a distal sidewall that is perpendicular with respect to an axis of the axial lumen;

a proximal sidewall having a beveled edge; and a bottom region connecting the distal sidewall and the beveled edge that is concentric with and of smaller diameter than the sealing surface, wherein the sealing surface has a constant diameter along a portion of its axial length and extends distally from the annular channel.

22. The dual lumen male bayonet connector of claim 21, further comprising a webbed portion formed between the first shaft and the second shaft that connects the first shaft to the second shaft in parallel.

23. The dual lumen male bayonet connector of claim 22, wherein the webbed portion is proximal to the annular channel.

24. The dual lumen male bayonet connector of claim 22, wherein a ratio of an axial length of the sealing surface to an axial distance between the distal sidewall of the annular channel and the webbed portion is between 0.889 and 1.105.

25. The dual lumen male bayonet connector of claim 22, wherein a distance between central axes of the axial lumen of the first and second shafts is between 1.695 to 2.035 times the distance between the distal sidewall and the webbed portion.

26. The dual lumen male bayonet connector of claim 22, wherein a ratio of the axial length of the sealing surface to an axial distance between the distal sidewall of the annular channel and the webbed portion is such that a side-load force of up to 10lbs, as imparted on the dual lumen male bayonet connector, will not break a fluid-tight seal between the sealing surface and the receiving portion of the female receiving structure.

27. The dual lumen male bayonet connector of claim 21, further comprising a rib extending between the first shaft and the second shaft.

\* \* \* \* \*